United States Patent
Duriot et al.

(10) Patent No.: US 11,311,593 B2
(45) Date of Patent: Apr. 26, 2022

(54) ROOT EXTRACTS FROM PLANTS OF THE MORUS GENUS AND USES OF SAME

(71) Applicant: PLANT ADVANCED TECHNOLOGIES PAT, Vandoeuvre-les-Nancy (FR)

(72) Inventors: Léonor Cécile Duriot, Saffais (FR); Aleksander Bogusz Salwinski, Nancy (FR); Léa Iolé Heidi Rangoni, Strasbourg (FR)

(73) Assignee: PLANT ADVANCED TECHNOLOGIES PAT, Vandoeuvre-les-Nancy (FR)

( * ) Notice: Subject to any disclaimer, the term of this patent is extended or adjusted under 35 U.S.C. 154(b) by 0 days.

(21) Appl. No.: 16/753,912

(22) PCT Filed: Oct. 4, 2018

(86) PCT No.: PCT/EP2018/077042
§ 371 (c)(1),
(2) Date: Apr. 6, 2020

(87) PCT Pub. No.: WO2019/068824
PCT Pub. Date: Apr. 11, 2019

(65) Prior Publication Data
US 2020/0360457 A1    Nov. 19, 2020

(30) Foreign Application Priority Data
Oct. 6, 2017 (FR) ..................................... 1759396

(51) Int. Cl.
| | |
|---|---|
| A61K 36/00 | (2006.01) |
| A61K 36/605 | (2006.01) |
| A23L 33/105 | (2016.01) |
| A61K 8/9789 | (2017.01) |
| A61P 17/02 | (2006.01) |
| A61K 8/49 | (2006.01) |
| A61K 31/343 | (2006.01) |
| A61K 31/352 | (2006.01) |
| A61K 31/353 | (2006.01) |
| A61Q 19/02 | (2006.01) |
| A61Q 19/08 | (2006.01) |

(52) U.S. Cl.
CPC .......... *A61K 36/605* (2013.01); *A23L 33/105* (2016.08); *A61K 8/498* (2013.01); *A61K 8/4973* (2013.01); *A61K 8/9789* (2017.08); *A61K 31/343* (2013.01); *A61K 31/352* (2013.01); *A61K 31/353* (2013.01); *A61P 17/02* (2018.01); *A61Q 19/02* (2013.01); *A61Q 19/08* (2013.01); A23V 2002/00 (2013.01); A61K 2236/11 (2013.01); A61K 2236/15 (2013.01); A61K 2236/17 (2013.01); A61K 2236/33 (2013.01); A61K 2236/53 (2013.01)

(58) Field of Classification Search
CPC .......................... A61Q 19/08; A23V 2200/318
See application file for complete search history.

(56) References Cited

U.S. PATENT DOCUMENTS

| | | |
|---|---|---|
| 5,164,182 A | 11/1992 | Meybeck et al. |
| 6,348,204 B1 | 2/2002 | Touzan |
| 7,350,331 B1 | 4/2008 | Gontier et al. |
| 7,919,658 B2 | 4/2011 | Adkesson et al. |
| 8,183,417 B2 | 5/2012 | Adkesson et al. |
| 9,844,576 B2 | 12/2017 | Brownell et al. |
| 2011/0152581 A1 | 6/2011 | Adkesson et al. |
| 2018/0099019 A1 | 4/2018 | Brownell et al. |
| 2019/0008757 A1 | 1/2019 | Leclere-Bienfait et al. |

FOREIGN PATENT DOCUMENTS

| | | | |
|---|---|---|---|
| CN | 101904809 A | * | 12/2010 |
| EP | 0997140 A1 | | 5/2000 |
| FR | 2616328 A1 | | 12/1988 |
| FR | 2868308 A1 | | 10/2005 |
| FR | 3056753 A1 | | 3/2018 |
| WO | 01/33942 A1 | | 5/2001 |
| WO | 2004/101479 A2 | | 11/2004 |
| WO | 2013/181296 A2 | | 12/2013 |
| WO | 2015/149136 A2 | | 10/2015 |
| WO | 2017/129779 A1 | | 8/2017 |

OTHER PUBLICATIONS

Nomura et al, Components of root bark of *Morus australis*. I. Structure of a new 2-arylbenzofuran derivative, mulberrofuran D. Planta Medica (1983), vol. 49, No. 2, pp. 90-94 (Year: 1983).*
Kang, Five new diels-alder type adducts from the stem and root bark of Morus mongolica. Planta medica, (Jan. 2006) vol. 72, No. 1, pp. 52-59 (Year: 2006).*
Yang, Y. et al., "The latest review on the polyphenols and their bioactivities of Chinese Morus plants," J Asian Nat Prod Res. 2014;16(6):690-702.
Jeong, J. et al., "Characterization of Melanogenesis Inhibitory Constituents of Morus alba Leaves and Optimization of Extraction Conditions Using Response Surface Methodology," Molecules, May 14, 2015;20(5):8730-41.
Tan, Y-X. et al., "Wittiorumins A-F, antioxidant Diels-Alder-type adducts from Morus wittiorum," Planta Med. Feb. 2009;75(3):249-55.

(Continued)

*Primary Examiner* — Qiuwen Mi
(74) *Attorney, Agent, or Firm* — Nixon & Vanderhye

(57) ABSTRACT

Disclosed is a root extract from plants of the *Morus* genus (in particular *Morus albaet*, *Morus nigra*) that is rich in prenylated polyphenols chosen from: moracenin A, moracenin B, kuwanon C, wittiorumin F and mulberrofuran T, a method for preparing such an extract and a cosmetic composition and a pharmaceutical or nutraceutical composition, the compositions including, as the active ingredient, at least one root extract from plants of the *Morus* genus according to the invention.

21 Claims, 6 Drawing Sheets

(56) References Cited

OTHER PUBLICATIONS

Kang, J. et al., "Five new Diels-Alder type adducts from the stem and root bark of Morus mongolica," Planta Med. Jan. 2006;72(1):52-9.

Livak, K. and Schmittgen, T., "Analysis of relative gene expression data using Real-Time Quantitative PCR and the 2-ΔCt method," Methods, 25 (4), 2001, 402-408.

Kang et al., "Prediction of tyrosinase inhibitory activities of Morus alba root bark extracts from HPLC fingerprints", Microchemical Journal, 2013, pp. 731-738, vol. 110, XP028737620.

Jeong et al., "Characterization of Melanogenesis Inhibitory Constituents of Morus alba Leaves and Optimization of Extraction Conditions Using Response Surface Methodology", Molecules, 2015, pp. 8730-8741, vol. 20, No. 5.

Pfaffl, "A new mathematical model for relative quantification in real-time RT-PCR", Nucleic Acids Research, 2001, pp. 2002-2007, vol. 29, No. 9.

Zheng et al., "Tyrosinase inhibitory constituents from the roots of Morus nigra: a structure-activity relationship study", Journal of Agricultural and Food Chemistry, 2010, pp. 5368-5373, vol. 58, No. 9, XP055479819.

Zheng et al., "Tyrosinase inhibition constituents from the roots of Morus australis", Fitoterapia, 2012, pp. 1008-1013, vol. 83, No. 6, XP028427381.

Dr. Sulochana Priya, "Medicinal Values of Mulberry—An Overview", Journal of Pharmacy Research, 2012, 3588-3596, vol. 5, No. 7, XP055479829.

International Search Report, dated Dec. 19, 2018, from corresponding PCT application No. PCT/EP2018/077042.

FR Search Report, dated Jun. 1, 2018, form corresponding FR application No. FR 1759396.

The First Office Action issued in CN Patent Application No. 1880064536.6, dated Sep. 1, 2021 with English translation provided.

Chaita et al., "Anti-Melanogenic Properties of Greek Plants. A Novel Depigmenting Agent from Morus alba Wood", Molecules 22(4): 514, Mar. 23, 2017, 14 pages.

\* cited by examiner

ROOT EXTRACTS FROM PLANTS OF THE MORUS GENUS AND USES OF SAME

FIELD OF THE INVENTION

The present invention pertains to the field of plant extracts and relates to a root extract of plants of the genus *Morus* (in particular *Morus alba* and *Morus nigra*) that are rich in prenylated polyphenols, to a method for the preparation of an extract of this type as well as to a cosmetic composition and a pharmaceutical or nutraceutical composition, said compositions comprising, as the active agent, at least one root extract of plants of the genus *Morus* in accordance with the invention.

PRIOR ART

Plants of the genus *Morus*, tree or bush, from the Moraceae family, may be sources of phenolic compounds with beneficial activities (The latest review on the polyphenols and their bioactivities of Chinese *Morus* plants; Yang Y. et al; J Asian Nat Prod Res. 2014; 16(6):690-702). The bark from the roots, stems and leaves of plants of the genus *Morus*, and in particular white mulberry, are traditionally used in Chinese medicine for the treatment of diabetes, arthritis or rheumatism. Among their many virtues, the extracts are known for their hypotensive, anti-inflammatory and antimicrobial activity. It has been shown that these properties are due to their polyphenol content, in particular resveratrol derivatives such as mulberroside A, Diels-Alder type adducts, and prenylated flavonoids of the moracenin or kuwanon type.

Tyrosinase is the enzyme limiting the rate of synthesis of melanin and it is the principal target for remedies countering hyperpigmentation. Extracts obtained from the roots, stems and leaves of *Morus alba, Morus nigra* and *Morus australis* are routinely used in the cosmetics industry as an agent for whitening the skin. These extracts contain compounds inhibiting the activity of the tyrosinase, such as moracenin A and moracenin B identified in the roots of *Morus nigra* (Tyrosinase inhibitory constituents from the roots of *Morus nigra*: a structure-activity relationship study; Zheng Z P et al; J Agric Food Chem. 2010 May 12; 58(9):5368-73) or in the root bark from *Morus alba* (Prediction of tyrosinase inhibitory activities of *Morus alba* root bark extracts from HPLC fingerprints; Kyo Bin Kang et al; Microchemical Daynal, 2013, 110, 731-738), or kuwanon C identified in leaves from *Morus alba* (Characterization of Melanogenesis Inhibitory Constituents of *Morus alba* Leaves and Optimization of Extraction Conditions Using Response Surface Methodology Molecules; Jeong J Y, et al; Molecules 2015 May 14; 20(5):8730-41).

Wittiorumin F and mulberrofuran T are Diels-Alder type adducts (adduct of a chalcone and a prenylated 2-arylbenzofuran). The first adduct was isolated from the bark of the stem of *Morus wittiorum* (Wittiorumins A-F, antioxidant Diels-Alder-type adducts from *Morus wittiorum*; Tan Y X et al; Planta Med. 2009 February;75(3):249-55) and the second adduct from callus tissue from *Morus alba* or in the root bark of *Morus mongolica* (Five new Diels-Alder type adducts from the stem and root bark of *Morus mongolica*; Kang J. et al; Planta Med. 2006 January;72(1):52-9). Application WO 2013/181296 describes a composition comprising Diels-Alder type adducts between a chalcone and a prenylphenylated group, and at least one other weight management agent for the treatment, prevention or management of weight gain in a mammal.

In order to meet the challenge of increasing demand in the fields of cosmetics and pharmaceuticals, there is a large amount of interest in identifying novel natural compounds that are capable of inhibiting the activity of tyrosinase highly effectively.

In order to satisfy this demand, the inventors have now developed a method that permits the preparation of a root extract of plants of the genus *Morus* that is rich in prenylated polyphenols. In fact, the inventors have shown that culturing plants of the genus *Morus*, in particular *Morus alba* and *Morus nigra*, under particular conditions, can be used to obtain a root extract of said plants that is rich in prenylated polyphenols with the presence of wittiorumin F and mulberrofuran T. The inventors have demonstrated an affinity for tyrosinase for these latter two compounds for the first time. Astonishingly, this affinity is stronger than that of inhibitors which are already known, such as moracenin A, moracenin B and kuwanon C. According to the results regarding affinity, wittiorumin F has the best inhibiting activity, followed by kuwanon C, then by moracenin B and A. Unexpectedly, moracenin A and B, kuwanon C, wittiorumin F and mulberrofuran T present in the root extract also have an affinity for collagenase, confirmed by the strong inhibiting activity of the extract as regards collagenase. Unexpectedly again, moracenin A and B, kuwanon C, wittiorumin F and mulberrofuran T present in the root extract also have an affinity for hyaluronidase, confirmed by the strong inhibiting activity of the extract as regards hyaluronidase, and especially the strong activity of moracenin A.

A method of this type can also be used to produce successive extractions without destroying or altering the survival of the plants.

Finally, the inventors have demonstrated that the root extract in accordance with the invention, in addition to its cosmetic benefits such as whitening or an anti-aging effect such as, for example, an effect on the strength, firmness, density, elasticity or in fact the smooth appearance of the skin (inhibition of hyaluronidase and inhibition of collagenase), may also be used as a drug in order to promote skin healing comprise closing of a wound.

DESCRIPTION OF THE FIGURES

In FIG. 3A, the numbered peaks respectively correspond to the compounds: moracenin B (1), kuwanon C (2), moracenin A (3), wittiorumin F (4) and mulberrofuran T (5).

In FIG. 4A, the numbered peaks respectively correspond to the compounds: moracenin B (1), kuwanon C (2), moracenin A (3), wittiorumin F (4) and mulberrofuran T (5).

In FIGS. 6A and 6B, the numbered peaks respectively correspond to the compounds: moracenin B (1), kuwanon C (2), moracenin A (3), wittiorumin F (4) and mulberrofuran T (5).

DETAILED DESCRIPTION OF THE INVENTION

Figures 1A, 1B, 1C:
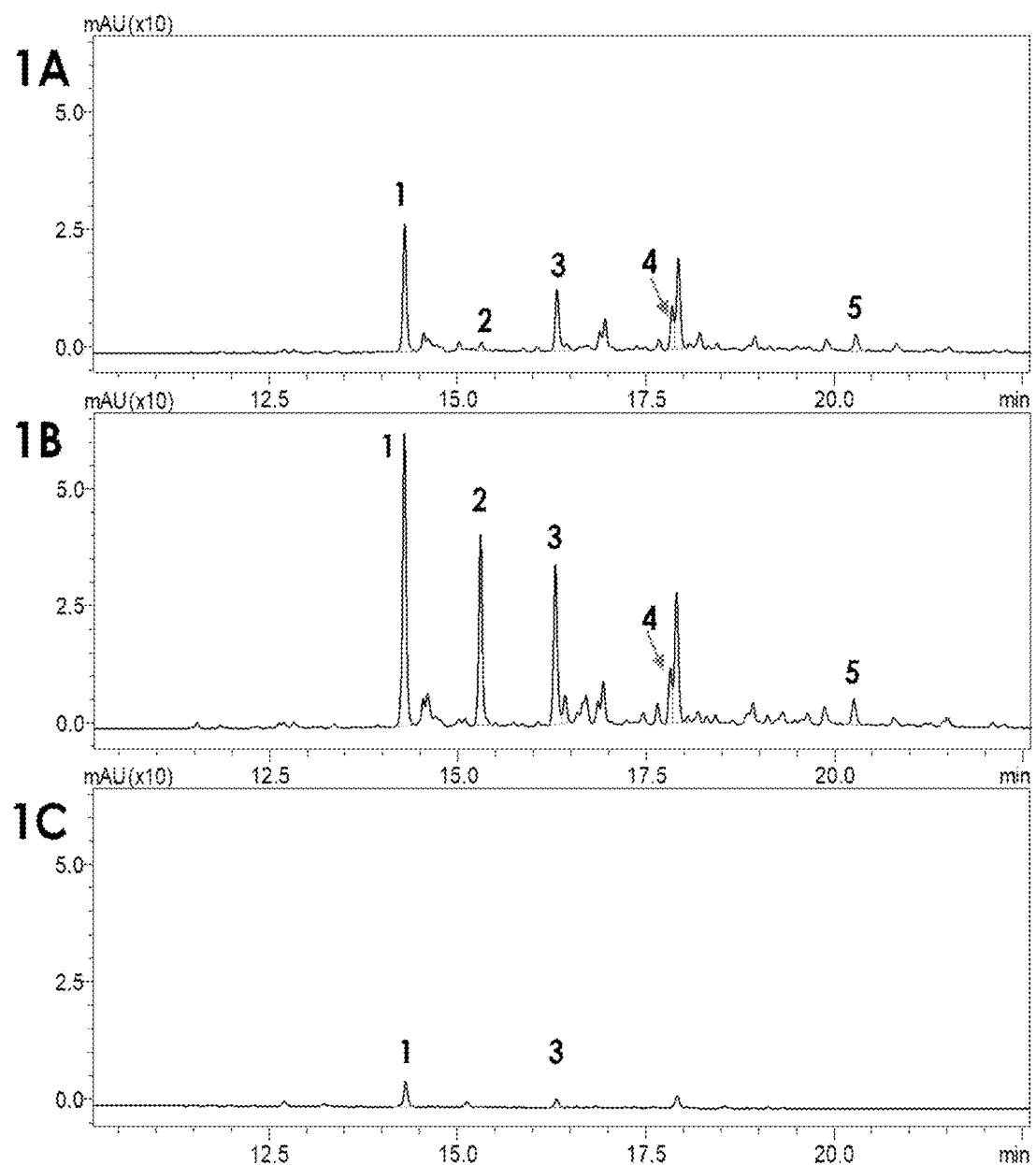
FIGS. 1A to 1C: Chromatograms (UV at 265 nm) of extracts prepared from roots of *M. alba*, not stimulated (FIG. 1A) or stimulated (FIG. 1B) or from dried root bark of *M. alba* (FIG. 1C), in accordance with Example 1, diluted 5-fold before injection. The peaks Nos 1, 2, 3, 4 and 5 correspond respectively to moracenin B, kuwanon C, moracenin A, wittiorumin F and mulberrofuran T, in accordance with Example 1.

The present invention concerns a root extract of plants of the genus *Morus*, characterized in that:
- it comprises at least 2% by weight of moracenin B, preferably at least 2.3%, at least 3%, at least 4%, at least 5%, at least 6% and more preferably at least 7%, expressed with respect to the total weight of the dry extract,
- it comprises moracenin A, in a quantity of at least 0.05% by weight in equivalents of moracenin B, preferably at least 0.1%, at least 0.5%, at least 1%, at least 1.5% and more preferably at least 2%, expressed with respect to the total weight of the dry extract,
- it comprises kuwanon C, in a quantity of at least 0.1% by weight in equivalents of moracenin B, preferably at least 0.5%, at least 1%, at least 1.5%, at least 2%, and more preferably at least 2.5%, expressed with respect to the total weight of the dry extract, and
- it comprises at least one of the following two compounds:
    - wittiorumin F, in a quantity of at least 0.1% by weight in equivalents of moracenin B, preferably at least 0.4%, at least 0.5%, at least 0.6%, at least 0.7% and more preferably at least 0.8%, expressed with respect to the total weight of the dry extract,
    - mulberrofuran T, in a quantity of at least 0.1% by weight, preferably at least 0.2%, at least 0.3%, at least 0.4% and more preferably at least 0.5%, expressed with respect to the total weight of the dry extract.

The term "root extract of plants of the genus *Morus*" means a product obtained by extraction from roots of plants of the genus *Morus*. Said extraction may be carried out by any means known to the person skilled in the art, and preferably by one of the means described in the present patent application. This preferably means a product obtained by the extraction from roots of plants of the genus *Morus* cultivated under soil-free conditions, and in particular aeroponically.

The term "prenylated derivatives of polyphenols" means the series of compounds moracenin B, moracenin A, kuwanon C, wittiorumin F and mulberrofuran T.

The term "moracenin B" (also known as kuwanon G) means a compound having the following general formula (I): $C_{40}H_{36}O_{11}$

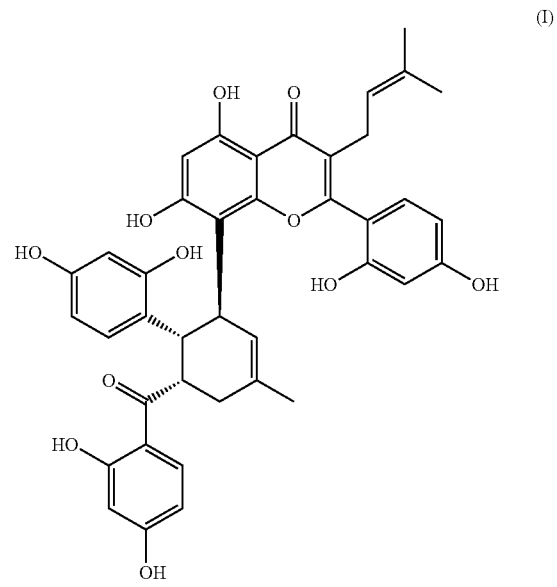

(I)

The term "moracenin A" (also known as kuwanon H or albalin G) means a compound having the following general formula (II): $C_{45}H_{44}O_{11}$

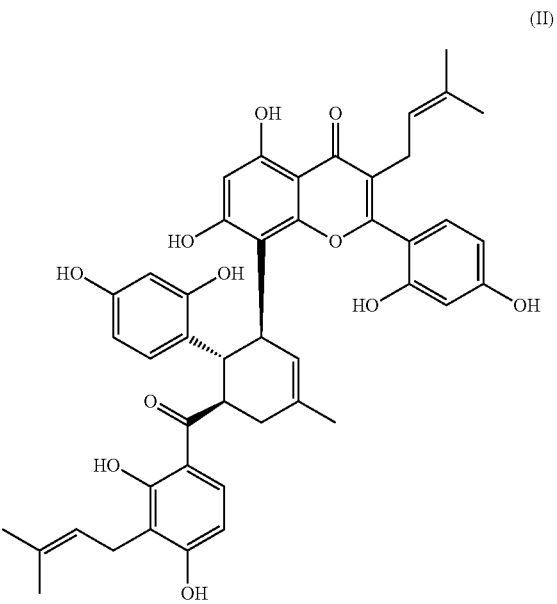

(II)

The term "kuwanon C" means a compound having the following general formula (III): $C_{25}H_{26}O_6$

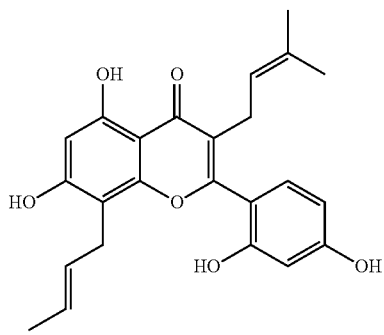

(III)

The term "wittiorumin F" means a compound having the following general formula (IV): $C_{39}H_{36}O_9$. (IV)

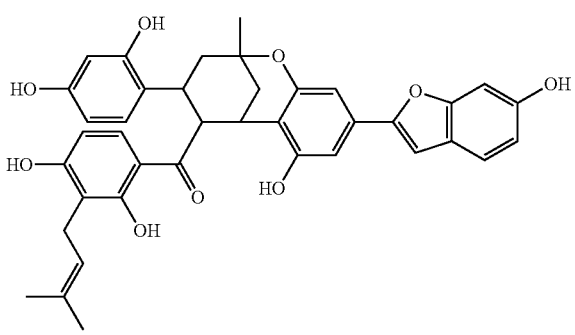

(IV)

The term "mulberrofuran T" means a compound having the following general formula (V): $C_{44}H_{44}O_9$

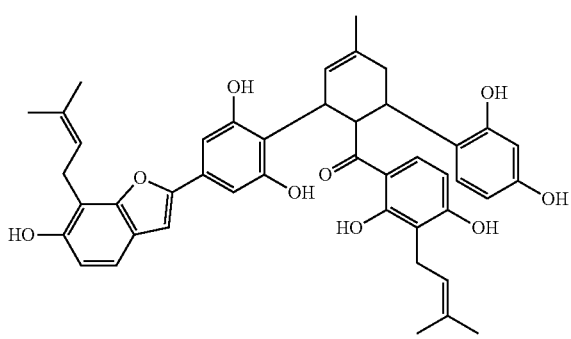

(V)

The term "dry extract" means an extract obtained by carrying out any type of extraction method, including a method in accordance with the invention, followed by a step for desiccation of the extract, the desiccation being carried out using any method which is well known to the person skilled in the art, in particular treatment of the extract in a hot, dry atmosphere.

In accordance with a preferred aspect, a "dry extract" is thus an extract obtained by carrying out the method in accordance with the invention followed by a step for desiccation of the extract.

The concentration in a root extract of a compound selected from: moracenin A, kuwanon C, wittiorumin F and mulberrofuran T is determined by measuring the area of the peak corresponding to said compound on the chromatogram for the HPLC analysis of said root extract: the area of said peak is related to the area of the peak corresponding to moracenin B on the chromatogram for the HPLC analysis of a standard solution comprising 100 mg/L of moracenin B; an "equivalent of moracenin B" is thus equal to:

$$100 \times \frac{\text{(area of peak corresponding to compound of the extract)}}{\left(\begin{array}{c}\text{area of peak corresponding to}\\ \text{moracenin } B \text{ of the standard solution}\end{array}\right)} [\text{mg/L}]$$

In order to obtain a root extract, when the roots are judged to be sufficiently developed, they are brought into contact with a solvent, optionally by immersion or, as is preferable, by maceration, and then said solvent is recovered and treated to extract from it the compounds of interest which have been released by the roots of said plants. This type of method is adapted from the method developed by Plant Advanced Technologies (PAT) under the name "PAT Plantes à Traire®" [Plant Milking®] and described in international application WO 01/33942.

In accordance with a preferred aspect, a root extract of plants of the genus *Morus* in accordance with the invention is a root extract of a plant of the genus *Morus* selected from *Morus alba* and *Morus nigra*. More preferably, it is a root extract of *Morus alba*. In accordance with a particular aspect, a root extract of plants of the genus *Morus* in accordance with the invention is a root extract of a plant of the genus *Morus* selected from *Morus alba* and *Morus nigra* cultivated under soil-free conditions, and in particular aeroponically.

In a second aspect, the invention concerns a method for the preparation of a root extract of plants of the genus *Morus* in accordance with the invention, comprising:

a) a step for culturing plants of the genus *Morus* under soil-free conditions, preferably aeroponically, b) optionally, a step for stimulation of the roots of the plants, c) a step for solid/liquid extraction of the roots, optionally stimulated during step b), and d) recovery of the extract obtained during step c).

In the context of the invention, the term "culture of plants under soil-free conditions" means any mode of culture in which the roots of the plant are not in the ground. More precisely, soil-free culture is cultivation in which the roots of the plants lie in a reconstituted medium, disconnected from the ground. This culture medium is irrigated in a regular manner by nutrient solutions that are appropriate for the cultivated plant.

Different soil-free culture techniques exist, such as substrate-free systems that require a nutrient solution enriched in oxygen, and systems with a substrate. Substrate-free systems that may be cited are aquiculture, in which the nutrient solution does not circulate and is contained in a culture tank, the Nutrient Film Technique or N.F.T., in which the nutrient solution becomes enriched in oxygen dissolved during its displacement by exchange with the air, and aeroponics. Systems with a substrate include subirrigation, in which the nutrient solution penetrates into the substrate at its lower portion, and percolation, in which the nutrient solution is distributed by discontinuous irrigation at the upper surface of the system then percolates towards the bottom of the substrate. The substrate, which may be mineral or organic, is neutral and inert, such as sand, clay or rock wool, for example. This substrate may also be of industrial origin.

The term "culture of plants aeroponically" means a soil-free culture mode in which the roots of the plants are not in contact with either a solid medium, or in fact with a liquid medium. In accordance with a particular embodiment, the plants are fed via a nutrient mist obtained by misting, using an atomizer, of the nutrient solution in a closed medium.

Typically, in a method in accordance with the invention, the plants may be disposed on plates with the aerial part of the plant above the plate and the root portion below, the plates are placed on tables forming a retaining zone in order to collect the surplus liquid dispersed towards the plants, and the plates are transferred onto tables with a variety of stations.

During step a), the aeroponically cultivated plants are fed by root spraying a nutrient solution of essential mineral salts (nitrogen—N, phosphorus—P, potassium—K), in order to obtain a maximum root development and a maximum concentration of compounds of interest without altering the survival of the plant. With the aid of their general knowledge, the person skilled in the art will know how to adapt the proportions and concentrations of the various mineral salts in order to optimize the root development and the concentration of the compounds of interest. The concentrations of mineral salts of the nutrient solutions are in this case included in a range of electroconductivity which advantageously is in the range 0.8 to 1.6 mS/cm, preferably in the range 1 to 1.2 mS/cm, in order to allow a maximum growth of the plant with a better yield of root biomass as well as in order to promote a higher content of prenylated polyphenols in the extracts.

In step c) of a method in accordance with the invention, the term "solid/liquid extraction" means any solvent extraction technique that consists of extracting a chemical species found in a solid and which is soluble in said solvent. Extraction techniques that may be cited are maceration, immersion, exudation, infusion, decoction, extraction using Soxhlet and Kumagawa extractors, microwave-assisted extraction, ultrasound-assisted extraction, enzymatic extraction, extraction using a supercritical fluid ($CO_2$+dipropylene glycol). The extraction leads to the recovery of metabolites contained in one or another part of the plants, and in particular the roots, by means of a leaching liquid or solvent, brought into contact with roots chopped up in a particular solvent and for an appropriate period of time.

In accordance with a particular aspect, in a method in accordance with the invention, the step c) for solid/liquid extraction of the roots, optionally stimulated during step b), is carried out by means of a maceration.

In accordance with a particular aspect, in a method in accordance with the invention, the step c) for solid/liquid extraction of the roots, optionally stimulated during step b), comprises chopping up the roots.

Typically, the plants are disposed on a plate with the aerial part of the plant above the plate and the root part below it. A chopping step in which the root portion of the plants is partially chopped up means that the chopped roots can be harvested. It is possible to extract the substances from the chopped roots.

In accordance with another preferred aspect, maceration of the roots is carried out on freshly chopped roots, i.e. chopped less than 24 hours previously, and preferably as soon as possible following chopping, ideally just after chopping. In particular, the root maceration may be carried out by means of a step for maceration of the freshly chopped roots in an appropriate solvent, at an appropriate pH, and for an appropriate period of time.

Preferably, maceration of the roots is carried out on chopped roots which may optionally also be dried. In accordance with a very particular aspect, the maceration of the roots is carried out on chopped roots, optionally dried, then crushed. The roots may be dried by carrying out any suitable drying process that is known to the person skilled in the art, and in particular by placing the roots at a temperature in the range 30° C. to 50° C. for 4 hours to 72 hours, preferably in a dry environment. The roots may in particular be dried in a ventilated oven. The roots may be crushed by carrying out any suitable crushing process that is known to the person skilled in the art, and in particular by placing the roots in a ball mill, a cutting mill or a cylinder crusher. As an example, the dried roots may be crushed until a powder is obtained.

More particularly, step c) of a method in accordance with the invention comprises bringing roots into the presence of a solvent selected from: alcohols, glycols and eutectic solvents. Said alcohol is preferably selected from ethanol and methanol, used pure or in the form of an aqueous solution of the alcohol, this comprising 10% to 99.9% of alcohol, more particularly between 40% and 90%, and yet more particularly between 50% and 85%. Said glycol is a diol in which the two hydroxyl groups are carried by different carbons, and is selected from: dipropylene glycol, propane-1,3-diol, propane-1,2-diol and butylene glycol, and is used pure or in the form of an aqueous glycol solution, this comprising 10% to 99.9% of glycol, more particularly between 40% and 90%, and yet more particularly between 50% and 85%. Said eutectic solvent is constituted by two or more components, which may be solid or liquid and which, in a particular composition, exhibit a large reduction in their fusion temperature, thereby rendering the mixture liquid. The natural eutectic solvents are principally constituted by amino adds, organic adds, sugars and choline derivatives. Water may form part of the solvent, but in this case, it is strongly retained in the liquid and cannot be evaporated. Particular combinations of components constituting said eutectic solvent are in particular, but not in an exhaustive manner, selected from choline chloride—glucose (ratio 1:1), choline chloride—citric acid (ratio 1:1), choline chloride—citric acid (ratio 2:1), choline chloride—saccharose (ratio 4:1), choline chloride—saccharose (ratio 1:1), choline chloride—tartaric acid (ratio 2:1), choline chloride—xylose (ratio 2:1), choline chloride—xylose (ratio 3:1), citric acid—saccharose (ratio 1:1), citric acid—glucose (ratio 1:1), glucose—tartaric acid (ratio 1:1), choline chloride—urea (ratio 1:2), choline chloride—xylitol—water (2:1:3) and lactic acid—glucose—water (5:1:3).

The term "butylene glycol" means butane-1,2-diol, butane-1,3-diol, butane-2,3-diol and butane-1,4-diol.

These solvents, and more particularly ethanol, butylene glycol, propane-1,3-diol and propane-1,2-diol, can be used to promote the extraction of a large quantity of prenylated polyphenols.

In the case of a mixture of at least two root extracts, the solvents present in said at least two extracts may be identical or different.

In accordance with a particular aspect of the invention, the solvent is characterized by a slightly acidic pH, in particular when it is used during the solid/liquid extraction step. In accordance with a particular aspect, said alcohol or said glycol used during a solid/liquid extraction step is characterized by a pH in the range 3.5 to 6.5, preferably a pH greater than or equal to 4 and less than or equal to 6.5, more preferably a pH greater than or equal to 4 and less than or equal to 6, yet more preferably a pH in the range 4 to 4.5. The use of a solvent with an acidic to slightly acidic pH, i.e. greater than or equal to 3.5 and less than or equal to 6.5, promotes dissolution of the compounds of interest in said solvent.

In accordance with another particular aspect, a plant extract after extraction in accordance with the invention is characterized by a pH in the range 5 to 7 and preferably in the range 5.5 to 6.5. A slightly acidic to neutral pH limits the chemical or enzymatic degradation of the prenylated polyphenols after the extraction.

The acids used to adjust the pH of the solvent or of the extract are preferably lactic acid, phosphoric acid, citric acid or hydrochloric acid.

More particularly, said glycol is selected from the following group: butylene glycol, propane-1,3-diol and propane-1,2-diol.

Propane-1,3-diol, or trimethylene glycol, may be prepared by chemical synthesis using techniques known to the person skilled in the art and described in the literature; it is also commercially available. Said propane-1,3-diol may also be produced by carrying out a fermentation process under conditions that are suitable for a living organism, in particular a genetically modified strain of *Escherichia coli*. The propane-1,3-diol obtained in this manner is designated by the term "biosourced propane-1,3-diol"; a product of this type is produced then purified as described in particular in the international application WO 2004/101479 and marketed under the trade name Zéméa). Said propane-1,3-diol may also have a biocertification, for example of the COSMOS type.

More particularly still, in a method in accordance with the invention, step c) for solid/liquid extraction comprises bringing the roots into the presence of propane-1,2-diol or with propane-1,3-diol, and in particular biosourced and/or biocertified propane-1,3-diol.

The root maceration periods are selected in a manner such as to promote the extraction of a large quantity of compounds of interest.

In accordance with a particular aspect, step c) of a method in accordance with the invention comprises bringing the roots into the presence of a solvent for a period in the range 5 minutes to 3 hours for the maceration of dried roots and for a period in the range 15 minutes to 96 hours, in particular between 24 hours and 72 hours, more particularly between 24 hours and 48 hours, for the maceration of fresh roots.

For the root maceration of fresh roots, the ratio of the quantity of fresh roots to the quantity of solvent varies between 0.2 kg of roots/L of solvent and 1 kg of roots/L of solvent.

In accordance with another particular aspect, a method in accordance with the invention comprises a step for drying freshly chopped roots, prior to the step for maceration of said roots, the maceration being carried out by bringing the dried roots into the presence of a solvent. For the root maceration, the ratio of the quantity of dried roots to the quantity of solvent varies between 0.01 kg of roots/L of solvent and 0.1 kg of roots/L of solvent.

Preferably, the step for maceration of the roots by bringing the roots into the presence of a solvent is carried out with stirring.

In accordance with a particular aspect, after the step for chopping the roots, the plants are cultured for 1 to 8 weeks aeroponically in accordance with the step a) and optionally undergo a step b) for stimulation for 1 day to 8 weeks in order to recommence their root development and promote the production of secondary metabolites by the roots.

In accordance with a preferred aspect, a method in accordance with the invention is a method for the preparation of a root extract of plants of the species *Morus alba* or of the species *Morus nigra*, more preferably of the species *Morus alba* or of the species *Morus nigra*, cultivated under soil-free conditions, and in particular aeroponically.

In accordance with a preferred embodiment, the invention also provides a method for the preparation of a root extract of plants of the genus *Morus* in accordance with the invention, comprising:

a) a step for culturing plants of the genus *Morus* under soil-free conditions, and in particular aeroponically,
b) a step for stimulation of the roots of the plants,
c) a step for solid/liquid extraction of the roots stimulated during step b), and
d) recovery of the extract obtained during step c).

In accordance with another particular aspect, in a method in accordance with the invention, the step b) for stimulation of the roots of the plants comprises:

a step for elicitation, in which the roots are brought into the presence of a solution comprising at least one agent selected from: a salt, a surfactant, a solvent, an elicitor of fungal, plant or bacterial origin, a derivative of jasmonic add, in particular methyl jasmonate, salicylic add, an ethylene generator, coronalone, a chitin, chitosans and/or a mixture thereof, and/or a step for bringing the roots into the presence of a solution that is deficient in nitrogen, i.e. a solution comprising a proportion of nitrogen which is less than the proportion of nitrogen usually considered to be optimal for the development of the plant, advantageously less than 15% of nitrogen, and advantageously containing no nitrogen, said steps being sequential or simultaneous.

The roots may also be stimulated by bringing the plants into the presence of a nutrient solution deficient in nitrogen. Bringing the plants into the presence of a nutrient solution that is deficient in nitrogen causes a "nitrogen stress" responsible for the stimulation. In accordance with a particular aspect, a solution deficient in nitrogen in accordance with the present invention is a solution comprising less than 15% of nitrogen, preferably less than 10% of nitrogen, advantageously less than 8%, more advantageously less than 6%, less than 5%, less than 4%, less than 3%, less than 2%, less than 1% of nitrogen and yet more advantageously 0% of nitrogen.

The step b) for stimulation may be used to significantly increase the secondary metabolites content in the roots and thereby promote the flow of metabolites leaving the roots into the solvent selected for the extraction, and indeed without a total loss of the viability of the plant, so that it can be re-cultivated then reused. In other words, the step for stimulation of the plant can be used to promote the production and secretion of the compounds of interest.

Advantageously, the step b) for stimulation of the roots is carried out by spraying or maceration of the plant with a solution of elicitors selected from: salicylic acid, coronalone and chitosans, or by feeding the plant with a N/P/K nutrient solution deficient in nitrogen vaporized onto the roots.

In accordance with a particular embodiment of the invention, step b) is carried out by spraying or maceration of the plant with a solution selected from:

a solution of corolanone in a concentration in the range 0.1 to 200 µM, advantageously between 1 and 100 µM,
a solution of salicylic acid in a concentration in the range 1 to 500 µM, advantageously between 10 and 50 µM, a solution of chitosans in a concentration of 0.002 to 1 g/L, advantageously of 0.05 to 0.1 g/L, and a N/P/K solution nutrient comprising less than 6% of nitrogen, said solution preferably being vaporized onto the roots.

In addition, step b) for stimulation of the roots with a solution of elicitors is advantageously carried out for a period in the range 1 day to 21 days, preferably between 1 and 7 days.

In accordance with a particular aspect, the step b) for stimulation of the roots by feeding the plant with a nutrient N/P/K solution that is deficient in nitrogen vaporized onto the roots is advantageously carried out for a period in the range 7 days to 8 weeks, preferably 3 weeks.

During step b), the concentrations of mineral salts in the nutrient solutions are in an electroconductivity range which advantageously is in the range 0.6 to 0.9 mS/cm, preferably between 0.6 and 0.8 mS/cm, in order to encourage a larger content of prenylated polyphenols in the extracts.

In accordance with a particular aspect of a method in accordance with the invention, step b) is carried out after step a). In accordance with another particular aspect of a method in accordance with the invention, step b) and step a) are carried out simultaneously; the stimulating solution is then incorporated into the nutrient solution or administered using any other mode of administration known to the person skilled in the art.

In accordance with an improvement, the step for "chopping" the roots is preceded by a step for washing, in which the liquid dispersed towards the roots is clean water. This thereby limits the addition of elements contained in the nutrient solution or in any stimulating solution during the solid/liquid extraction step.

Advantageously, the invention provides a method for the preparation of a root extract of plants of the genus *Morus*, comprising the following steps:

a) a step for culturing plants of the genus *Morus* under soil-free conditions, and in particular aeroponically, b) a step for stimulation of the roots of the plants, c) a step for solid/liquid extraction of the roots, stimulated during step b), comprising chopping, drying and crushing said roots, followed by maceration of the crushed roots in a solvent, said solvent being selected from: alcohols, glycols and eutectic solvents, and being used pure or in the form of an aqueous solution of alcohol, of glycol or of eutectic solvent, and d) the recovery of the extracts obtained during step c).

In accordance with a particular aspect, in a method in accordance with the invention, the pH of the solvent is in the range 3.5 to 6.5, preferably between 3.5 and 6, preferably between 3.5 and 5, more preferably between 4 and 4.5.

A method in accordance with the invention advantageously comprises a supplemental step for readjusting the content of solvent in the extract, in order to obtain an advantageous content of at least 50%, and/or an adjustment of the pH of the extract, in order to obtain a pH that is advantageously in the range 3 to 7, preferably in the range 4 to 6.5, with a view to preservation of the extract.

A method in accordance with the invention advantageously comprises at least one supplemental step for purification and/or for treatment of the root extract; a step of this type is in particular selected from:

at least one filtration, in particular a nanofiltration and/or a sterilizing filtration and/or a clarifying filtration, a liquid/solid extraction, a purification, a concentration and a decolorization of the root extract, such purification and/or treatment methods being well known to the person skilled in the art. This step may be used to obtain the final extract of *Morus*, preferably of *Morus alba* or *Morus nigra*, which is rich in prenylated polyphenols, in particular in moracenin B, in moracenin A, in kuwanon C, in wittiorumin F and in mulberrofuran T.

Figure 5:
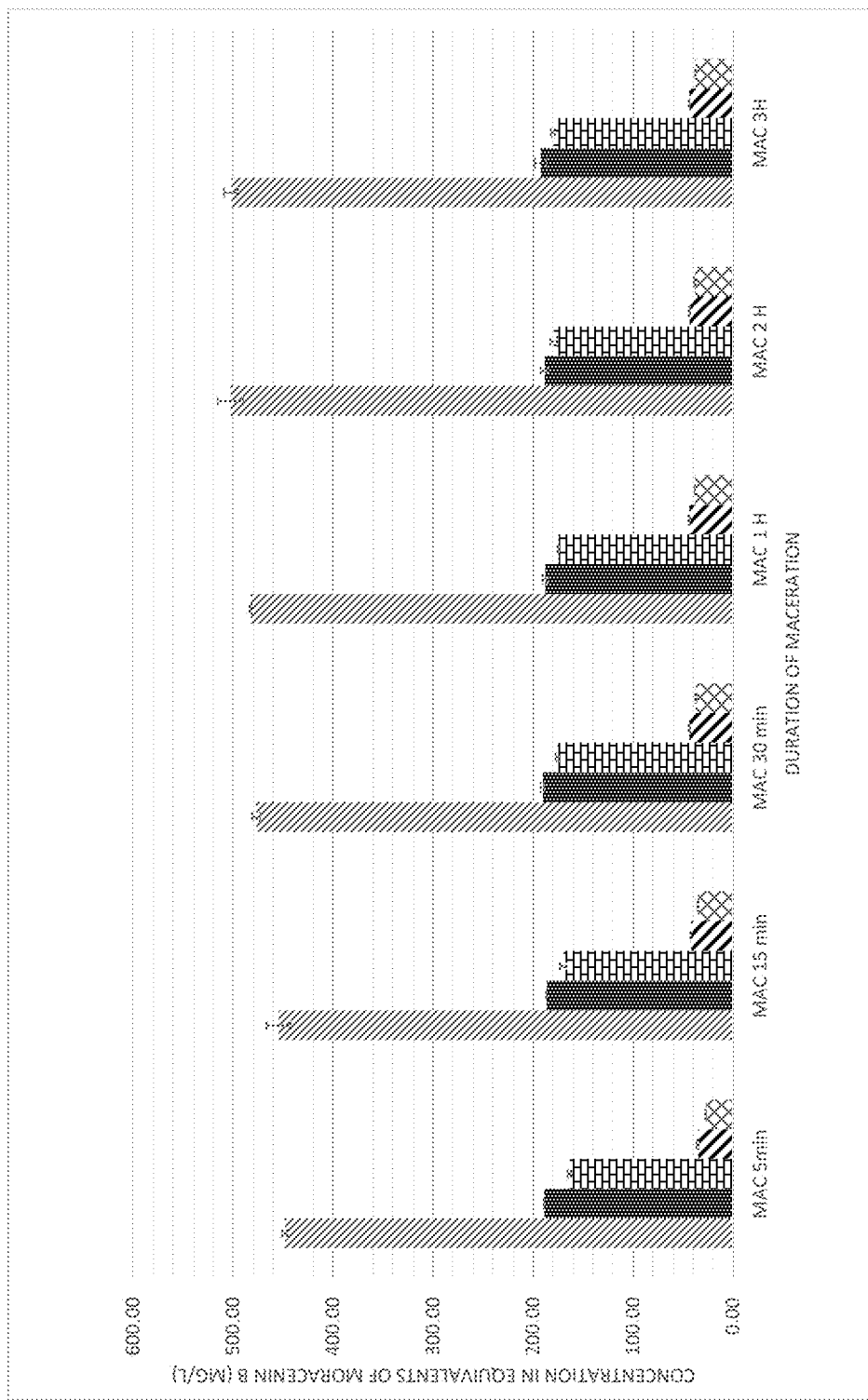
FIG. 5: Histogram showing the contents of moracenin B as well as for moracenin A, kuwanon C, wittiorumin F and mulberrofuran T, expressed in equivalents of moracenin B, in the root extract stimulated of *M. alba* as a function of the duration of root maceration, in accordance with Example 5. For each of the maceration conditions, the respective concentrations (in mg/L) of moracenin B, kuwanon C (in equivalents of moracenin B), moracenin A (in equivalents of moracenin B), wittiorumin F (in equivalents of moracenin B), mulberrofuran T (in equivalents of moracenin B) are indicated from left to right.

FIG. 5 shows the different concentrations of moracenin B, of kuwanon C, of moracenin A, of wittiorumin F and of mulberrofuran T in a root extract of *M. alba* as a function of the duration of maceration in accordance with the invention.

The present invention also provides a root extract that is capable of being obtained by a method in accordance with the invention.

A third aim of the present invention is to provide a cosmetic composition comprising, as the active agent, at least one root extract in accordance with the invention or a root extract obtained by a method in accordance with the invention, and at least a cosmetically acceptable excipient. Advantageously, said root extract is an extract of plants of the genus *Morus*, preferably *Morus alba* or *Morus nigra*. More preferentially, it is a root extract of *Morus alba*. In accordance with a particular aspect, a root extract of plants of the genus *Morus* is a root extract of a plant of the genus *Morus* selected from *Morus alba* or *Morus nigra* cultivated under soil-free conditions, and in particular aeroponically.

The modes of administration, the dosages and the optimal galenical forms of a cosmetic composition in accordance with the invention may be determined in accordance with the criteria generally taken into account when developing a cosmetic treatment that is suitable for a subject, such as the type of skin, for example.

The cosmetic composition in accordance with the invention is advantageously intended for topical application. It may in particular be in the form of a cream, a milk, a lotion, a gel, a serum, a spray, a foam, a solution, an ointment, an emulsion, a patch or a mask. A cosmetic composition in accordance with the invention comprises at least one cosmetically acceptable excipient selected as a function of the desired type of administration. A cosmetic composition in accordance with the present invention may furthermore comprise at least one adjuvant known to the person skilled in the art, selected from thickeners, preservatives, fragrances, colorants, chemical or mineral filters, moisturizing agents, spa water, etc.

A cosmetically acceptable excipient may be selected from polymers, silicone compounds, surfactants, rheological agents, humectants, penetration agents, oily components, waxes, emulsifiers, film-forming agents, fragrances, electrolytes, pH adjusters, antioxidants, preservatives, colorants, nacres, pigments and mixtures thereof.

A cosmetic composition in accordance with the invention may furthermore comprise at least one other cosmetically active agent such as another anti-aging agent, a moisturizing agent, an agent having a calming, soothing or relaxing activity, an agent stimulating cutaneous microcirculation, a sebo-regulating agent for the care of oily skin, a cleansing or purifying agent, a free radical scavenger, an anti-inflammatory agent, a chemical or mineral sunscreen, etc.

Advantageously, a cosmetic composition in accordance with the invention comprises at least one root extract of *Morus* in accordance with the invention, and in particular a root extract of *Morus alba* or of *Morus nigra* in accordance with the invention, in a quantity in the range 0.01% to 10%, in particular between 0.05% and 5%, more particularly between 0.1% and 2%, by weight with respect to the total weight of the composition.

A cosmetic composition in accordance with the invention may in particular be intended to have a whitening effect on the skin, in particular by inhibiting the activity of tyrosinase.

A cosmetic composition in accordance with the invention may also be intended to have an anti-aging effect, in particular by inhibiting the activity of hyaluronidase and/or by inhibiting the activity of collagenase.

In a fourth aspect, the present invention provides a root extract in accordance with the invention, a root extract obtained by a method in accordance with the invention, or a cosmetic composition in accordance with the invention, for preventing or retarding the appearance of the effects of aging of the skin by stimulating the barrier function of the epidermis and/or by inhibiting the activity of hyaluronidase, and/or by inhibiting the activity of collagenase, and/or may have a whitening effect on the skin.

The present invention also concerns the use of an extract in accordance with the invention, an extract obtained by a method in accordance with the invention for the preparation of a cosmetic composition intended to prevent or retard the appearance of the effects of aging of the skin and/or intended to provide the skin with a whitening effect.

The present invention also concerns a method for the cosmetic care of the skin, intended to prevent or retard the appearance of the effects of aging of the skin, by stimulating the barrier function of the epidermis, and/or by inhibiting the activity of hyaluronidase and/or by inhibiting the activity of collagenase, and/or intended to provide the skin with a whitening effect, said method being characterized in that it comprises the application, to at least a portion of the skin of the body or the face, of a cosmetic composition in accordance with the invention.

A fifth aim of the present invention is to provide a pharmaceutical composition comprising, as the active agent, at least one extract in accordance with the invention or an extract obtained by a method in accordance with the invention, and at least one pharmaceutically acceptable excipient.

A sixth aim of the present invention is to provide a nutraceutical composition comprising, as the active agent, at least one extract in accordance with the invention or an extract obtained by a method in accordance with the invention, and at least one nutraceutically acceptable excipient.

In the present invention, the term "pharmaceutically or nutraceutically acceptable" means any ingredient which is useful in the preparation of a pharmaceutical or nutraceutical composition, which is generally safe, non-toxic and neither biologically nor otherwise undesirable and which is acceptable for veterinary use or for human application.

The terms "pharmaceutically or nutraceutically acceptable salts" of a compound means salts which are pharmaceutically or nutraceutically acceptable, as defined above, and which have the desired pharmacological activity of the parent compound. Salts of this type include:

(1) hydrates and solvates,
(2) addition salts of pharmaceutically or nutraceutically acceptable adds formed with pharmaceutically or nutraceutically acceptable inorganic acids such as hydrochloric acid, hydrobromic acid, sulfuric acid, nitric acid, phosphoric acid and the like; or formed with pharmaceutically or nutraceutically acceptable organic acids such as acetic acid, benzenesulfonic acid, benzoic acid, camphorsulfonic acid, citric acid, ethanesulfonic acid, fumaric acid, glucoheptonic add, gluconic acid, glutamic add, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic add, propionic acid, salicylic acid, succinic acid, dibenzoyl-L-tartaric acid, tartaric acid, p-toluenesulfonic acid, trimethylacetic acid, trifluocoacetic acid and the like, or
(3) the addition salts of pharmaceutically or nutraceutically acceptable bases formed when a protonic add present in the parent compound is either replaced by a metal ion, for example an alkali metal ion, an alkaline earth metal ion or an aluminum ion; or coordinated with a pharmaceutically or nutraceutically acceptable organic or inorganic base. The acceptable organic bases include diethanolamine, ethanolamine, N-methylglucamine, triethanolamine, tromethamine and the like. Acceptable inorganic bases include aluminum hydroxide, calcium hydroxide, potassium hydroxide, sodium carbonate and sodium hydroxide.

The modes of administration, the dosages and the optimal galenical forms of a pharmaceutical composition in accordance with the invention may be determined in accordance with the criteria generally taken into account when developing a pharmaceutical treatment that is suitable for a subject such as, for example, the age or body weight of the patient, the seriousness of the condition, tolerance to the treatment, known side effects, skin type. Depending on the type of administration desired, the pharmaceutical composition in accordance with the invention may also comprise at least one pharmaceutically acceptable excipient. The pharmaceutical composition in accordance with the present invention may furthermore comprise at least one pharmaceutical adjuvant that is known to the person skilled in the art, selected from thickeners, preservatives, fragrances, colorants, chemical or mineral filters, moisturizers, spa water, etc.

Advantageously, said pharmaceutical composition comprises at least one extract in accordance with the invention in a quantity in the range 0.01% to 10%, in particular between 0.05% and 5%, more particularly between 0.1% and 2%, by weight with respect to the total weight of the composition.

A pharmaceutical composition is particularly suitable for administration orally, nasally, transdermally, parenterally, topically, rectally and mucosally. It may be in the dry form, such as, for example: a soft capsule, gelule, tablet, lyophilizate, powder, granule or patch, or in the liquid form, such as: solution, suspension, spray, cream or gel.

The pharmaceutically acceptable excipient is known to the person skilled in the art and is selected as a function of the mode of administration of the pharmaceutical composition. By way of example, the pharmaceutically acceptable excipient may be selected from the group constituted by diluents, binders, disintegrants, colorants, lubricants, solubilizing agents, absorption promoting agents, film-forming agents, gelling agents and mixtures thereof.

The pharmaceutical composition in accordance with the invention may furthermore comprise at least one compound selected from the group constituted by emollients, moisturizing agents, keratin synthesis activators, keratoregulators, keratolytics, agents restructuring the skin barrier (activators of the synthesis of skin lipids, PPAR or Peroxysome Proliferator Activated Receptor agonists), keratinocyte differentiation activators (retinoids, Calcidone®, calcium), antibiotics, antibacterial agents, antifungal compounds, antiviral agents, seboregulators, immunomodulators, such as tacrolimus, pimecrolimus, oxazolines, preservatives, anti-irritants, soothing agents, sunscreens and filters, antioxidants, growth factors, healing agents or eutrophic molecules, anti-inflammatory drugs and agents, and anti-Alzheimer drugs and agents A seventh aim of the present invention is to provide an extract in accordance with the invention or a pharmaceutical composition in accordance with the invention, for use thereof as a drug.

More particularly, the present invention also concerns an extract in accordance with the invention, an extract obtained by the method in accordance with the invention, or a pharmaceutical composition in accordance with the invention, for use thereof as a drug in order to promote skin healing comprise closing of a wound. Said extract will advantageously be associated with a pharmaceutically acceptable excipient that is suitable for application to the skin, and said pharmaceutical composition will advantageously contain a pharmaceutically acceptable excipient that is suitable for application to the skin.

More particularly, the present invention also concerns an extract in accordance with the invention, an extract obtained using a method in accordance with the invention, or a pharmaceutical composition in accordance with the invention, for use thereof as a drug in order to stimulate and/or improve firmness, density, strength, the smooth appearance and/or the elasticity of the skin. Said extract will advantageously be associated with a pharmaceutically acceptable excipient that is suitable for application to the skin, and said pharmaceutical composition will advantageously contain a pharmaceutically acceptable excipient that is suitable for application to the skin.

The stimulation and/or improvement to the firmness, the density, the strength, the smooth appearance and/or the elasticity of the skin are in particular due to the inhibition of the activity of hyaluronidase and/or the inhibition of the activity of collagenase.

The invention also concerns a method for the therapeutic care of the skin in order to stimulate and/or improve the firmness, density, strength, the smooth appearance and/or the elasticity of the skin and/or to promote skin healing, in particular in the case of the closing of a wound, in a subject in need thereof, comprising administration to the subject of a therapeutically effective quantity of a nutraceutical composition in accordance with the invention or of a pharmaceutical composition in accordance with the invention.

The invention also concerns a method for the cosmetic care of the skin in order to promote whitening of the skin and/or to prevent or retard the appearance of the effects of aging (anti-aging effect), comprising the administration to a subject of a cosmetically effective quantity of a cosmetic composition in accordance with the invention.

Examples 1 to 7 below and FIGS. 1 to 6 are intended to illustrate the invention without, however, limiting its scope.

EXAMPLES

The root extracts of *Morus alba* were prepared from plants the seeds of which were purchased from a French supplier (Les Semences du Puy) from 2012 to 2015. The root extracts of *Morus nigra* were prepared from plants the seeds of which were purchased from a French supplier (Naudet Pépinières) in 2016. Since 2016, the plants of *Morus alba* and of *Morus nigra* have been preserved and propagated under glass by the Applicant.

Example 1

Phytochemical Profile of a Root Extract of *Morus Alba* and of *Morus Nigra* Before and After Stimulation

*Morus alba* plants were cultivated aeroponically for 8 weeks with a 15/10/30 (N/P/K) culture medium and with an electroconductivity in the range 1.0 to 1.2 mS/cm, then with a defined nutrient solution, with an N/P/K composition corresponding to 0/15/40 and with an electroconductivity in the range 0.6 to 0.8 mS/cm for 3 weeks. The roots were harvested before changing the medium and they corresponded to the non-stimulated roots.

Roots chopped and harvested before and after stimulation with deficient nitrogen were dried for 48 hours at 40° C. in a ventilated oven and crushed with the aid of a bead mill (WWR Star Beater) for 4 minutes at a speed of 15 beats per second. 20 mg of roots crushed to a powder were macerated in 1 mL of pure ethanol with stirring (using a vortex mixer) at ambient temperature for 30 minutes. The samples were centrifuged at 21000 g for 10 minutes in order to separate the solid material. The supernatants were recovered and diluted 5-fold in pure ethanol for injection.

The instrument used for the analysis step was a UPLC Shimadzu Nexera X2 (LC-30AD pumps, SIL-30AC autosampler, CTO-20A oven, SPD-M20A photodiode array detector; Kyoto, Japan) operated in reverse phase with a Kinetex EVO C18 column (00F-4725-AN, Phenomenex, Torrance, Calif., USA) with dimensions of 150 mm×2.1 mm, 2.6 µm. The mobile phase was constituted by a solvent A (Mili-Q Ultrapure Water, Merck Millipore+0.1% formic acid, Carlo Erba, Val-de-Reuil, France) and a solvent B (Acetonitrile, Sigma-Aldrich Chemie GmbH, Steinheim, Germany), wherein the gradient was programmed as follows: phase B (%) 5-72.5% (0-22 min); 72.5-90% (22-22.1 min); 90% (22.1-23.9 min), 90-5% (23.9-24 min), 5% (24-26 min). The flow rate for analysis was 0.5 mL/min with an oven temperature of 40° C. At the outlet from the column, a photodiode array detector recorded the UV spectra between 220 and 370 nm. The instrument was coupled to a mass spectrometer (Shimadzu LCMS-2020) operating with an electrospray ionization (4.5 kV) in negative mode in a m/z range between 200 and 1000. LabSolutions (version 5.60 SP2) software was used to operate the system.

The quantification of moracenin B was carried out by measuring the area of the peak for a moracenin B standard obtained by the Applicant from a root extract of *Morus alba* resulting from the maceration of 500 g of fresh roots in 1 liter of a 70/30 (ethanol/water—v/v) hydroethanolic solution for 48 hours. Briefly, the purified fraction of moracenin B was obtained by a phase separation method followed by preparative HPLC. Next, the fraction was characterized by HPLC followed by NMR. The moracenin B standard was prepared in a concentration of 100 mg/L in a DMSO/water mixture in the ratio 70/30 and acidified to a pH of 4 with hydrochloric add. The contents for the other compounds (moracenin A, kuwanon C, wittiorumin F and mulberrofuran T) are expressed in equivalents of moracenin B in each extract. The content was calculated using the following formula for a compound:

$$\text{Content of compound in mg/L} = 100 \times \frac{\begin{pmatrix} \text{area of peak} \\ \text{corresponding to} \\ \text{compound of} \\ \text{the extract} \end{pmatrix}}{\begin{pmatrix} \text{area of peak} \\ \text{corresponding to} \\ \text{moracenin } B \text{ of} \\ \text{the standard solution} \end{pmatrix}} [\text{mg/L}]$$

Moracenin B was used as the quantification standard for the various compounds (moracenin A, moracenin B, kuwanon C, wittiorumin F and mulberrofuran T) because these various compounds belong to the same family of molecules.

FIGS. 1A, 1B and 1C show the chromatograms of extracts prepared from roots of *M. alba*, not stimulated (FIG. 1A) or stimulated (FIG. 1B) and diluted 5-fold before injection. The dry extract content (DE) was evaluated to be 2.6 g/L for the *M. alba* extracts produced from stimulated roots and 2.3 g/L for the *M. alba* extracts produced from non-stimulated roots.

The contents for the compounds are indicated in Table 1 below.

TABLE 1

| Compound | *M. alba* extract | Content, in eq. of moracenin B, (mg/L) for 20 mg of crushed dried roots | | Content, in eq. of moracenin B, as % DE Value |
|---|---|---|---|---|
| | | Value | Standard deviation, n = 3 | |
| Moracenin B | Roots, stimulated | 126.1 | 3.1 | 4.8 |
| | Roots, not stimulated | 53.5 | 1.2 | 2.3 |
| Kuwanon C | Roots, stimulated | 83.2 | 1.6 | 3.2 |
| | Roots, not stimulated | 3.4 | 0.1 | 0.15 |
| Moracenin A | Roots, stimulated | 73.8 | 1.1 | 2.8 |
| | Roots, not stimulated | 28.5 | 0.7 | 1.2 |
| Wittiorumin F | Roots, stimulated | 22.8 | 0.6 | 0.9 |
| | Roots, not stimulated | 18.1 | 0.7 | 0.8 |
| Mulberrofuran T | Roots, stimulated | 13 | 0.5 | 0.5 |
| | Roots, not stimulated | 9.3 | 0.4 | 0.4 |

In the present example, the stimulation of roots of *M. alba* by nitrogen deficiency resulted in an increase in the content in the root extract (in mg/L):
of 136% of moracenin B
of 2358% of kuwanon C
of 159% of moracenin A
of 26% of wittiorumin F
of 39% of mulberrofuran T In order to verify that the root extract of *M. alba* in accordance with the invention was rich in prenylated polyphenols, i.e. that the root extract in accordance with the invention comprised a large quantity of moracenin B, moracenin A, kuwanon C, wittiorumin F and mulberrofuran T compared with a corresponding extract obtained from root bark from plants of the genus *Morus* which were commercially available, the phytochemical profile of an extract of dried root bark of *M. alba* (also known as Cortex Mori Albae Radicis or Sang Bai Pi) was produced. This bark (of Chinese origin, ordered by the Applicant in 2015) was in the form of thick, pale yellow-colored chips. The bark was crushed to reduce it to the state of a powder using a ball mill (WWR Star Beater) for 5 minutes at a speed of 20 beats per second and another 5 minutes at a speed of 30 beats per second. 20 mg of crushed Sang Bai Pi was macerated in 1 mL of pure ethanol, with stirring (using a vortex mixer) at ambient temperature for 30 minutes. The samples were centrifuged at 21000 g for 10 minutes in order to separate the solid material. The supernatants were recovered and diluted 5-fold in pure ethanol for injection. FIG. 1C shows the chromatogram of the extract prepared from bark. The dry extract (DE) content in the extracts was evaluated to be 0.63 g/L.

The quantification of the prenylated polyphenols was carried out using the protocol described below and the values are indicated in Table 2 below:

TABLE 2

| Compound | Content, in eq. of moracenin B (mg/L) for 20 mg of bark from dried roots of *M. alba* | | Content, in eq. of moracenin B as % of dry extract Value |
|---|---|---|---|
| | Value | Standard deviation, n = 3 | |
| Moracenin B | 11.74 | 0.34 | 1.86 |
| Moracenin A | 0.16 | 0.04 | 0.025 |
| Kuwanon C | 3.86 | 0.22 | 0.61 |
| Wittiorumin F | 0 | 0 | 0 |
| Mulberrofuran T | 0 | 0 | 0 |

The extract in accordance with the invention was characterized by the presence of wittiorumin F and of mulberrofuran T, which were not detected in the commercial bark extract, by very high moracenin A and B contents and by high kuwanon C contents for the stimulated roots.

The presence of wittiorumin F and of mulberrofuran T was confirmed in root extracts of *Morus nigra* prepared in accordance with the same protocol used to obtain extracts of *Morus alba* and described in the present example. The dry extract (DE) content was evaluated to be 2.67 g/L for the extract of *M. nigra* produced from roots stimulated for 4 weeks and to be 3.16 g/L for the extract of *M. nigra* produced from non-stimulated roots.

The quantification of the prenylated polyphenols was carried out in accordance with the protocol described below and the values (n=1) are indicated in Table 3 below:

TABLE 3

| Compound | Extract of *M. nigra* | Content, in eq. of moracenin B (mg/L), for 20 mg of crushed dried roots | Content, in eq. of moracenin B, as % DE |
|---|---|---|---|
| Wittiorumin F | Roots, stimulated | 25 | 0.93 |
| | Roots, not stimulated | 8 | 0.25 |
| Mulberrofuran T | Roots, stimulated | 13 | 0.48 |
| | Roots, not stimulated | 5 | 0.16 |

In the present example, the stimulation of roots of *M. nigra* by nitrogen deficiency resulted in an increase in the content in the root extract (in mg/L):
of 212% of wittiorumin F
of 160% of mulberrofuran T

Example 2

Anti-Tyrosinase Inhibiting Activity of a Root Extract of *Morus Alba*

2.1 Anti-Tyrosinase Inhibiting Activity on Non-Stimulated Roots of *M. alba*

*Morus alba* plants were cultivated aeroponically for 8 weeks with a 15/10/30 (N/P/K) culture medium and with an electroconductivity in the range 1.0 and 1.2 mS/cm. The roots were chopped, dried, crushed and macerated in pure ethanol in a ratio of 1 mL of ethanol for 20 mg dry matter in accordance with the protocol described in Example 1. The sample was centrifuged at 21000 g for 10 minutes in order to separate the solid material. The anti-tyrosinase inhibiting activity of the supernatant was measured using L-tyrosine as the substrate. Tyrosinase catalyzes the conversion of L-tyrosine to dopaquinone, which is spontaneously converted into dopachrome. This latter absorbs strongly in the visible range of the electromagnetic spectrum (at 475 nm). The activity of the tyrosinase was measured by following the enzymatic conversion of the colorless L-tyrosine into orange dopachrome with the aid of a microplate reader.

The anti-tyrosinase activity of the supernatant was measured by mixing the following components: 150 µL of the solution of L-tyrosine (1.5 mM) in 50 mM sodium phosphate buffer, pH 6.8; 40 µL of supernatant diluted 2- to 800-fold in ethanol was tested as the inhibitor solution. The enzymatic conversion was initialized by adding a volume of 10 µL of fungal tyrosinase (0.2 mg/mL in a 50 mM sodium phosphate buffer, pH 6.8). The "control" experiment was carried out in the same manner, replacing the supernatant with pure ethanol.

Figure 2:
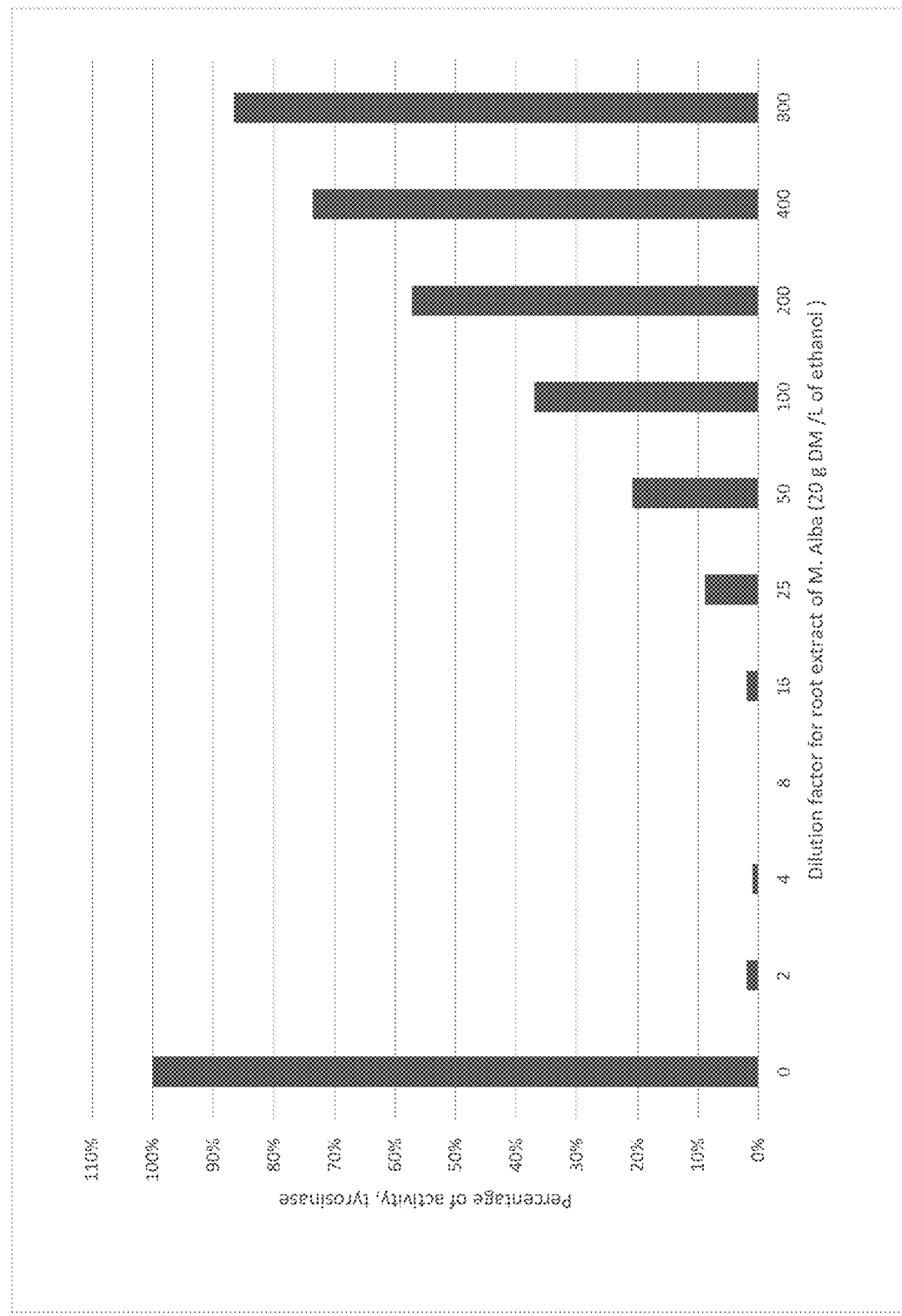
FIG. 2: Histogram showing the percentage activity of tyrosinase as a function of dilution factor for a non-stimulated root extract of *M. alba*, in accordance with Example 2. The median inhibiting concentration ($IC_{50}$) was evaluated for the dilution factor 150, which corresponds to an extract prepared from 0.13 mg of dry matter in 1 mL of pure ethanol.

FIG. 2 shows the percentage tyrosinase activity as a function of dilution factor of the supernatant. For dilutions in the range 2 to 16, almost complete inhibition of the activity was observed. The median inhibiting concentration C150 was evaluated for the dilution factor of 150, which corresponded to an extract prepared from 0.133 mg dry matter in 1 mL of pure ethanol. Starting from the data in Table 1 (Example 1, non-stimulated roots of *M. alba*), the contents in equivalents of moracenin B (mg/L) were calculated for the 5 prenylated polyphenols contained in an extract prepared from 133 mg of dried root of *M. alba* in 1 L of ethanol, i.e.:

0.36 mg/L of moracenin B
0.02 mg/L of kuwanon C, expressed in equivalents of moracenin B
0.19 mg/L of moracenin A, expressed in equivalents of moracenin B
0.12 mg/L of wittiorumin F, expressed in equivalents of moracenin B
0.06 mg/L of mulberrofuran T, expressed in equivalents of moracenin B 2.2 Comparison of Anti-Tyrosinase Inhibiting Activity on roots of *M. alba*, not Stimulated and Stimulated by Nitrogen Deficiency.

Two root extracts of *Morus alba* were prepared in accordance with the protocol described in Example 1. The measurement of the anti-tyrosinase inhibiting activity was carried out in accordance with the protocol described in Example 2.1 with 40 µL of each of the two extracts diluted 100-fold or 200-fold in pure ethanol.

Table 4 below presents shows the percentage inhibition of tyrosinase activity for each of the root extracts.

TABLE 4

| Dilution factor | Type of *M. alba* roots | Percentage inhibition of tyrosinase activity |
|---|---|---|
| 100 | stimulated | 86% |
|  | not stimulated | 70% |
| 200 | stimulated | 77% |
|  | not stimulated | 49% |

The extract prepared from roots stimulated by nitrogen deficiency inhibited the tyrosinase activity more strongly (86% and 77%) than the extract prepared from non-stimulated roots (70% and 49%).

2.3 Evaluation of the Affinity of Compounds Present in a Root Extract of *M. alba* for the Tyrosinase Target: Affinity Test by Target Binding®

A root extract of *Morus alba* was prepared in accordance with the protocol described in Example 2.1.

The Target Binding® method described in patent application FR 1 670 545 corresponds to a method for determining the affinity between ligands and a target. It is based on the principle of bringing the ligands and the target into contact in the liquid phase so that the ligands that have the greatest affinity with the target bind to it, elimination of the ligands that are not fixed, separation of the complexes in order to recover the ligands which have been fixed, then quantification of the latter.

In a first step of the method, the extract and the target are mixed. The compounds of the extract compete for access to the binding sites of the target. The strongest compounds displace the weakest and are retained more effectively by the target.

Subsequently, the following steps are carried out:
i) separation of the ligand-target complexes from the mixture;
ii) elimination of the compounds that have not been bound;
iii) denaturing of the ligand-target complexes in order to release the ligands;
iv) elimination of the denatured target by precipitation and centrifuging;
v) analysis of the supernatant: comparison of the analytical signals for the ligands of the supernatant with the analytical signals of the ligands for the sample.

The target, a 1.5 mg/mL solution of fungal tyrosinase, was prepared by dissolving lyophilized enzyme powder in 50 mM of ammonium acetate with a pH of 7.0. The sample to be analyzed corresponded to the supernatant of the root extract obtained in accordance with Example 2.1. it could optionally be centrifuged once again before use, at 21000 g for 15 min, in order to remove all traces of solid particles. A reference sample was also prepared by diluting the sample to be analyzed 10-fold in a solution of water and a quarter of the volume of acetonitrile.

The steps of the method were as follows:
1. Pre-conditioning step—Wells with a filtering membrane were pre-conditioned with a volume of 500 µL of an 85% solution of ammonium acetate and 15% of ethanol which was passed through the membrane by centrifuging at 14000 g for 60 seconds.
2. Binding step—The tyrosinase preparation (1.5 mg/mL, 92.5 µL) was mixed with 7.5 µL of the sample to be analyzed, for 5 min in a plastic Eppendorf tube.
3. Washing step—The mixture of the enzyme and the sample to be analyzed was deposited in a well that had been pre-conditioned in the pre-conditioning step, then centrifuged at 14000 g until most of the solvent had been eliminated. The enzyme-ligand complexes remained on the surface of the filter membrane, then were re-suspended in a volume of 100 µL of the same 85% ammonium acetate solution and 15% of ethanol and centrifuged at 14000 g until the solvent had been eliminated. This procedure was repeated three times and eliminated all of the compounds that were not bound to the enzyme.

4. Separation step—The enzyme-ligand complexes retained in the filter were re-suspended in a volume of 10 µL of ultra-pure water, then mixed with a volume of 40 µL of acetonitrile in order to denature and precipitate the enzyme and, at the same time, to liberate the ligands. The mixture was centrifuged at 21000 g for 10 min in order to separate the precipitate from the supernatant.

5. Analysis step—Said supernatant was analyzed by liquid phase chromatography coupled to a mass spectrometer, also known by the acronym UPLC-MS. The reference sample was also analyzed in the same manner, using the same analytical conditions.

The UPLC-MS analysis was carried out in accordance with the protocol described in Example 1.

Figures 3A, 3B:
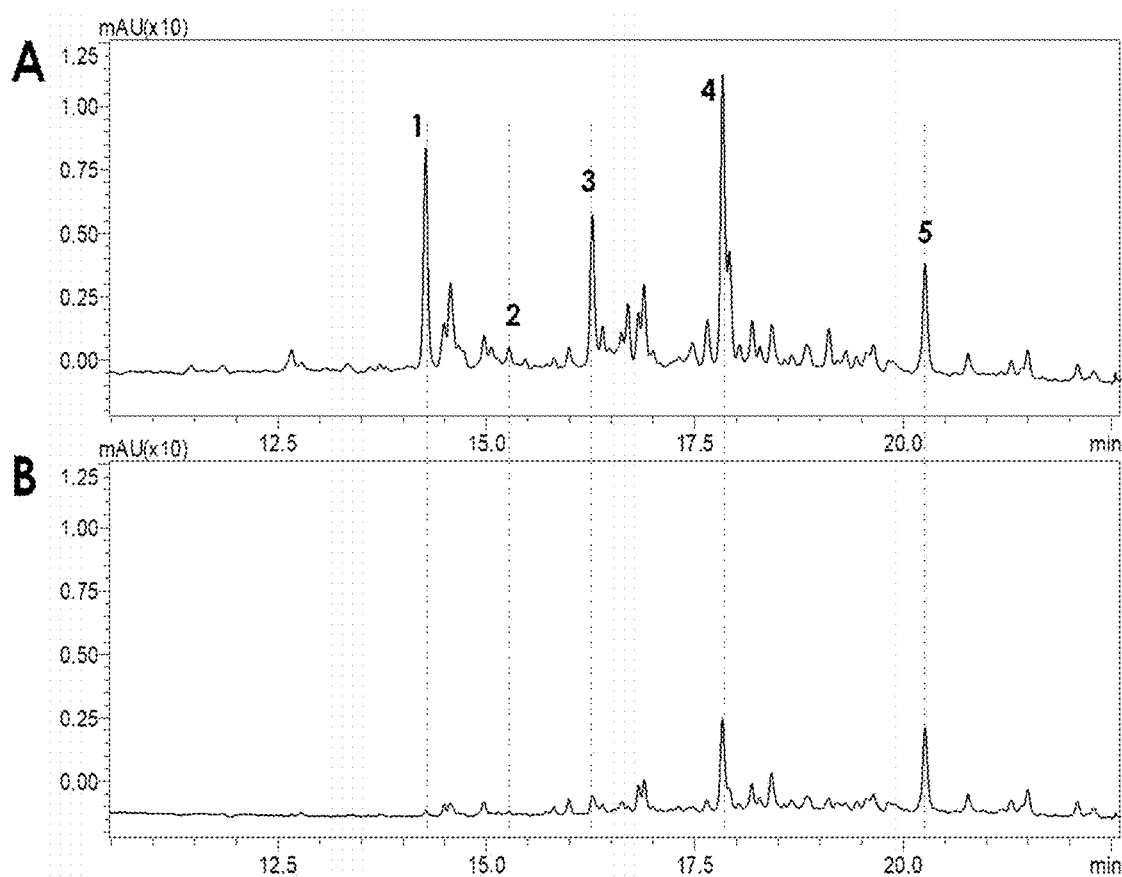
FIGS. 3A and 3B: Chromatograms (UV at 290 nm) for a reference sample (FIG. 3A) and the supernatant obtained in accordance with Example 2.3 during the evaluation of the affinity of a non-stimulated root extract of *M. alba* for tyrosinase, using the method known as Target Binding® described in patent application FR 1 670 545 (FIG. 3B).

The chromatograms obtained are presented in FIGS. 3A and 3B and represent a signal intensity as a function of retention time in a column. The signal shows various peaks with a variable intensity. Each peak is associated with one of the ligands present in the analyzed extract. The quantity associated with each ligand corresponds to the area of the peak.

The chromatogram (FIG. 3A) for the reference sample enabled the major compounds present in the root extract to be identified, namely:

1—moracenin B;
2—kuwanon C;
3—moracenin A;
4—wittiorumin F;
5—mulberrofuran T;

The comparison of the sizes of the areas of the peaks of the chromatogram of FIG. 3B obtained after binding of the compounds of the sample to be analyzed to the tyrosinase enabled a rough evaluation of the order of the affinity of the compounds of the root extract in accordance with Example 2.1 for tyrosinase to be made: the area of the peak was higher for mulberrofuran T and wittiorumin F, demonstrating a greater affinity for these two compounds.

In order to validate this result, the relative affinities were calculated using the method described in patent application FR 1 670 545.

For each ligand, an affinity ratio, RACEi, was calculated as follows:

$$RA_{CEi} = \frac{NF_{TB,CEi}}{NF_{eq,CEi}}$$

with:

$$NF_{eq,CEi} = \frac{IS_{eq,CEi}}{IS_{eq,REF}} \text{ and } NF_{TB,CEi} = \frac{IS_{TB,CEi}}{IS_{TB,REF}}$$

where:
NF is a normalization factor;
ISeq,CEi is the intensity of the analytical signal for the ligand CEi in the reference sample;
ISeq,REF is the intensity of the analytical signal for the reference ligand REF (here, moracenin B) in the reference sample;
ISTB,CEi is the intensity of the analytical signal for the ligand CEi in the treated solution (the sample to be analyzed after steps 2 to 4 for binding and separation of the ligands) for the detached ligands;
ISTB,REF is the intensity of the analytical signal for the reference ligand REF (here, moracenin B) in the treated solution (the sample to be analyzed after steps 2 to 4 for binding and separation of the ligands) for the detached ligands;
RA, CEi is the relative affinity ratio (RA), representing an affinity of the ligand CEi for the target. The value of the ratio increases with affinity.

TABLE 5

Relative affinity of moracenin B (considered to be the reference ligand), moracenin A, kuwanon C, wittiorumin F and mulberrofuran T present in the root extract of *M. alba* in accordance with Example 2.1 for tyrosinase.
Relative affinity (RA) for tyrosinase

| Moracenin B (reference) | Kuwanon C | Moracenin A | Wittiorumin F | Mulberrofuran T |
|---|---|---|---|---|
| 1.0 | 4.0 | 5.1 | 15.5 | 36.2 |

The relative affinities confirm the results based on the evaluation of the peak areas, namely a greater affinity for tyrosinase for mulberrofuran T and wittiorumin F compared with the other compounds that were evaluated.

Example 3

Anti-Collagenase Inhibiting Activity of a Root Extract of *Morus Alba*

3.1 Comparison of Anti-Collagenase Inhibiting Activity on Roots of *M. alba*, not Stimulated and Stimulated by Nitrogen Deficiency.

Two root extracts of *Morus alba* were prepared in accordance with the protocol described in Example 1. The measurement of the anti-collagenase inhibiting activity was carried out in accordance with the following protocol. The anti-collagenase inhibiting activity of the two extracts was measured using FALGPA (N-[3-(2-furyl)acryloyl]-Leu-Gly-Pro-Ala) as the substrate. Collagenase catalyzes the conversion of FALGPA into FAL (N-(3[2-furyl]acryloyl)-Leu) and Gly-Pro-Ala. The degradation of FALGPA is the source of a reduction in the absorption of the reaction mixture at 345 nm. The activity of the collagenase was measured by following the enzymatic conversion of the FALGPA into FAL+Gly-Pro-Ala with the aid of a UV-VIS spectrophotometer.

The reaction mixture as follows: 510 µL of the solution of FALGPA (1.5 mM) in 50 mM Tris-HCl buffer, 10 mM $CaCl_2$, 400 mM NaCl, pH 7.5; 30 µL of each of the two extracts, diluted 5-fold in pure ethanol was tested as an inhibitor solution. The enzymatic conversion was initialized by adding a volume of 10 µL of collagenase obtained from *Clostridium Histolyticum* (0.8 mg/mL in 50 mM Tris-HCl buffer, 10 mM $CaCl_2$, 400 mM NaCl, pH 7.5. The "control" experiment was carried out in the same manner, replacing the supernatant with pure ethanol.

The extract prepared from roots stimulated by nitrogen deficiency inhibited the collagenase activity (94%) more strongly than the extract prepared from non-stimulated roots (83%).

3.2 Evaluation of the Affinity of the Compounds Present in a Root Extract of *M. alba* for the Target Collagenase: Affinity Test by Target Binding®

A root extract of *Morus alba* was prepared in accordance with the protocol described in Example 2.1. The Target Binding® method used was that of Example 2.3 which is described in patent application FR 1 670 545. The experimental protocol was as follows:

The target, a 6.25 mg/mL solution of collagenase obtained from *Clostridium histolyticum*, was prepared by dissolving lyophilized enzyme powder in 50 mM saline phosphate buffer with a pH of 7.5. The sample to be analyzed corresponded to the supernatant of the root extract obtained in accordance with Example 2.1. It could be centrifuged once again before use, at 21000 g for 15 min, in order to remove any traces of solid particles. A reference sample was also prepared by diluting the sample to be analyzed 10-fold in a solution of water and a quarter of the volume of acetonitrile.

The steps of the method were as follows:
1.2. Analysis of the Sample
1. Preconditioning step—Wells with a filtering membrane were preconditioned with a volume of 500 µL of a saline phosphate buffer which was passed through the membrane by centrifuging at 14000 g for 60 seconds.
2. Binding step—A volume of 92.5 µL of the solution obtained from the pretreatment step was mixed with 7.5 µL of the sample to be analyzed for 10 min in a plastic Eppendorf tube.
3. Washing step—The mixture of the enzyme and the sample to be analyzed was deposited in a well that had been preconditioned in the preconditioning step, then centrifuged at 14000 g until most of the solvent had been eliminated. The enzyme-ligand complexes remained on the surface of the filter membrane, then were re-suspended in a volume of 100 µL of the same saline phosphate buffer solution and centrifuged at 14000 g until the solvent had been eliminated. This procedure was repeated three times and eliminated all of the compounds that were not bound to the enzyme.
4. Separation step—The enzyme-ligand complexes retained in the filter were re-suspended in a volume of 10 µL of ultra-pure water then mixed with a volume of 30 µL of acetonitrile in order to denature and precipitate the enzyme and, at the same time, to liberate the ligands. The mixture was centrifuged at 21000 g for 10 min in order to separate the precipitate from the supernatant.
5. Analysis step—Said supernatant was analyzed by liquid phase chromatography coupled to a mass spectrometer. The reference sample was also analyzed in the same manner, using the same analytical conditions.

The UPLC-MS analysis was carried out in accordance with the protocol described in Example 1.

The chromatogram (FIG. 4A) of the reference sample enabled the major compounds present in the root extract in accordance with Example 2.1 to be identified, namely:
1—moracenin B;
2—kuwanon C;
3—moracenin A;
4—wittiorumin F;
5—mulberrofuran T.

Figures 4A, 4B:
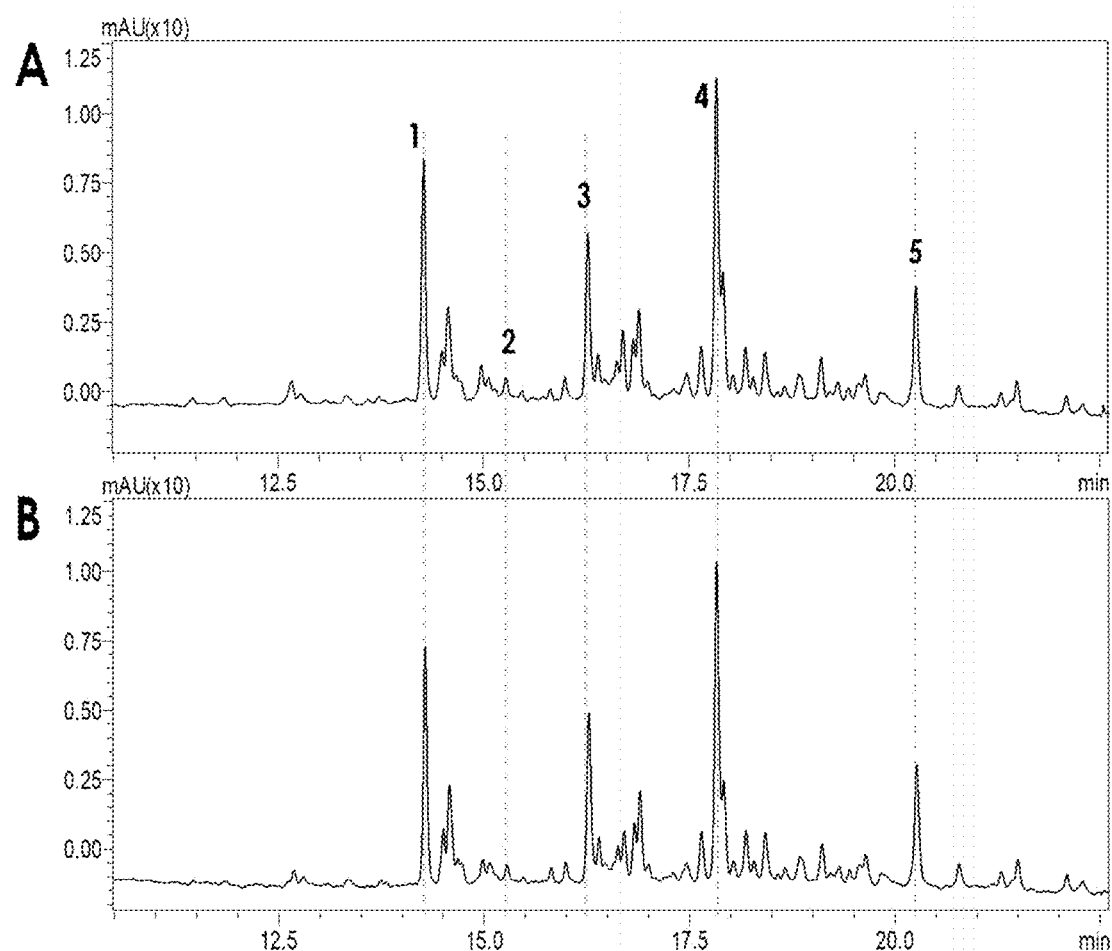
FIGS. 4A and 4B: Chromatograms (UV at 290 nm) for a reference sample (FIG. 4A) and the supernatant obtained in accordance with Example 3.2 during the evaluation of the affinity of a non-stimulated root extract of *M. alba* for collagenase, using the method known as Target Binding® (FIG. 4B).

The size of the areas of the peaks of the chromatogram of FIG. 4B after binding the compounds of the extract to the collagenase could be used to demonstrate a similar affinity of mulberrofuran T, wittiorumin F and moracenin A and B for collagenase.

In order to validate this result, the relative affinities were calculated in accordance with the method of Example 2.3 and described in patent application FR 1 670 545.

TABLE 6

Relative affinity of moracenin B (considered to be the reference ligand), moracenin A, kuwanon C, wittiorumin F and mulberrofuran T present in the root extract of *M. alba* with respect to collagenase. The relative affinities with respect to collagenase were similar for the 5 compounds.

Relative affinity (RA) for collagenase

| Moracenin B (reference) | Kuwanon C | Moracenin A | Wittiorumin F | Mulberrofuran T |
|---|---|---|---|---|
| 1.0 | 0.9 | 1.1 | 1.1 | 1.1 |

Example 4

Anti-Tyronisase Inhibiting Activity of Molecules Purified from Roots of *Morus Alba* and of *Morus Nigra*

Wittiorumin F was purified from a root extract of *Morus nigra* cultivated aeroponically, then stimulated by a nitrogen stress by using a nutrient medium without nitrogen (medium 0/15/40) for 2 to 6 weeks. 500 g of fresh roots were macerated in 1 liter of a 70/30 hydroethanolic solution (ethanol/water—v/v) for 48 hours. The pH of the maceration medium was not adjusted. Briefly, the purified fraction of wittiorumin F was obtained by preparative HPLC and characterized by NMR.

The moracenin A, moracenin B and kuwanon C were purified from a root extract of *Morus alba* in accordance with the protocol described in Example 1.

The measurement of the anti-tyrosinase inhibiting activity was carried out in accordance with the protocol described in Example 2.1.

The inhibiting activity for tyrosinase was tested for the 4 compounds at 3 concentrations and the results are presented in the Table below:

TABLE 7

Percentage inhibiting activity for tyrosinase for the 4 compounds at concentrations of 2.5 µM, 5 µM and 20 µM.

| Compound | Concentration 2.5 µM | | Concentration 5 µM | | Concentration 20 µM | |
|---|---|---|---|---|---|---|
| | % inhibition | Concentration mg/L | % inhibition | Concentration mg/L | % inhibition | Concentration mg/L |
| Moracenin A | 18.9% | 1.9 | 27.7% | 3.8 | 59.0% | 15.2 |
| Moracenin B | 22.6% | 1.7 | 33.5% | 3.5 | 69.7% | 13.9 |
| Kuwanon C | 24.7% | 1.1 | 37.7% | 2.1 | 72.7% | 8.4 |
| Wittiorumin F | 35.7% | 1.6 | 52.9% | 3.2 | 75.1% | 13 |

Wittiorumin F had the best inhibiting activity, followed by kuwanon C, then moracenin B and A. This result was in agreement with Example 2.3 showing a higher affinity for wittiorumin F for the target tyrosinase compared with the 3 prenylated flavonoids.

In Example 2.1, the median inhibiting concentration IC50 for tyrosinase was measured for an extract prepared from 133 mg of dried roots of *Morus alba* in 1 L of pure ethanol, corresponding to a total of 0.69 mg/L of moracenin B and A, kuwanon C and wittiorumin F, expressed in equivalents of moracenin B. For wittiorumin F, which was the most inhibiting compound, an inhibition of 52.9% was measured at a concentration of 3.2 mg/L. This comparison demonstrated a greater inhibiting activity for the root extract than for the isolated compounds.

Example 5

Root Extract of *Morus Alba* Prepared from a Glycolated Solvent

A root extract of *Morus alba* that was rich in prenylated polyphenols was obtained using the following method:
Culture of *Morus alba* aeroponically with a defined nutrient solution, with an N/P/K composition corresponding to 15/10/30 and with an electroconductivity in the range 1.0 and 1.2 mS/cm,
Stimulation of the plant for a period of 2 to 4 weeks by a nitrogen stress by using a N/P/K nutrient solution comprising: less than 6% of nitrogen, 15% of phosphorus and 40% of potassium, and with an electroconductivity of 0.6 to 0.8 mS/cm,
Extraction of compounds of interest by maceration of roots which had been chopped and dried and crushed with a planetary ball mill (Fritsch—PULVERISETTE 6), for a period in the range 5 minutes to 3 hours in a propane-1,3-diol/water mixture in accordance with a ratio in the range 85/15 to 70/30, at ambient temperature and at a pH in the range 3.5 to 4.5. The maceration was carried out at ambient temperature, with stirring. The dry matter (DM)/solvent ratio used for the maceration was 50 g DM/L of solvent. The maceration was carried out in a volume of 30 mL of solvent.

The contents for moracenin B as well as for moracenin A, kuwanon C, wittiorumin F and mulberrofuran T, expressed in equivalents of moracenin B in the root extract of *Morus alba* as a function of the maceration period, evaluated in accordance with the method described in Example 1, are indicated in FIG. 5.

The extracts obtained thereby had the following characteristics:
dry extract content: 7.1 g/L to 10.2 g/L
moracenin B content: 446 mg/L to 512 mg/L (i.e. 4.9% to 6.3% of the dry extract)
moracenin A content, expressed in equivalents of moracenin B: 162 mg/L to 182 mg/L (i.e. 1.7% to 2.3% of dry extract)
kuwanon C content, expressed in equivalents of moracenin B: 184 mg/L to 196 mg/L (i.e. 1.8% to 2.7% of dry extract)
wittiorumin F content, expressed in equivalents of moracenin B: 34 mg/L to 44.5 mg/L (i.e. 0.4% to 0.5% of dry extract)
mulberrofuran T content, expressed in equivalents of moracenin B: 27 mg/L to 29 mg/L (i.e. 0.38% to 0.41% of dry extract)
pH: 6+/−1

Two other root extracts of *Morus alba* that were rich in prenylated polyphenols were obtained using the following method:
The steps for culture and for stimulation of *Morus alba* were carried out in accordance with the protocol described above in the present Example 1.
The extraction of the compounds of interest was carried out by maceration of the chopped, dried and crushed (using a cutting mill) roots, for a period of 2 hours in a propane-1,3-diol/water mixture in accordance with a ratio in the range 85/15 to 70/30, at ambient temperature and at a pH of 4 or at a pH that had not been adjusted. The maceration was carried out at ambient temperature, with stirring with the aid of a planetary stirrer. The ratio of dry matter (DM)/solvent used for the maceration was 50 g DM/L of solvent. The maceration was carried out in a volume of 500 mL of solvent.

The contents for moracenin B as well as for moracenin A, kuwanon C, wittiorumin F and mulberrofuran T, expressed in equivalents of moracenin B, were evaluated in accordance with the method described in Example 1 and are presented in Table 8 below:

TABLE 8

Contents for dry extract, moracenin A as well as for moracenin B, kuwanon C, wittiorumin F and mulberrofuran T, expressed in equivalents of moracenin B and indicated in mg/L or as a % of dry extract (DE) for two root extracts of *Morus alba* obtained after maceration for two hours at a pH of 4 or at a pH that had not been adjusted.

| | Dry extract content (DE) g/L | Moracenin A mg/L | Moracenin A % DE | Moracenin B mg/L | Moracenin B & DE | Kuwanon C mg/L | Kuwanon C & DE | Wittiorumin F mg/L | Wittiorumin F & DE | Mulberrofuran T mg/L | Mulberrofuran T & DE |
|---|---|---|---|---|---|---|---|---|---|---|---|
| pH = 4 | 5 | 114 | 2.3 | 395 | 7.9 | 106 | 2.1 | 20 | 0.4 | 16 | 0.31 |
| pH not adjusted | 5.1 | 122 | 2.4 | 421 | 8.25 | 112 | 2.2 | 22 | 0.42 | 17 | 0.33 |

Example 6

Anti-Hyaluronidase Inhibiting Activity of a Root Extract of *Morus Alba*

Hyaluronic acid (HA) is a glycosaminoglycan which forms the extracellular matrix. It is produced by HASs (Hyaluronic Acid Synthases) and fills the intercellular spaces of the skin in order to maintain tissue cohesion and ensure its hydration by retaining molecules of water. Hyaluronidase catalyzes the hydrolysis of HA. With age or following repeated exposure to UV, the expression of this enzyme increases, causing a reduction in the quantity of hyaluronic acid in the skin. Thus, there is a genuine interest in inhibiting this enzyme with the aim of preventing or retarding the appearance of the effects of aging (anti-aging effect).

6.1 Test for Anti-Hyaluronidase Inhibiting Activity on Stimulated Roots of *M. alba*

A root extract of *Morus Alba* was prepared in accordance with the protocol described in Example 5. Hyaluronidase catalyzes the hydrolysis of hyaluronic acids into monosaccharides, disaccharides and short oligosaccharides. The measurement of the anti-hyaluronidase inhibiting activity was carried out using hyaluronic acid (HA) as a substrate in order to follow its reduction during the enzymatic reaction, the slope of the reduction of the concentration of HA during the reaction being proportional to the enzymatic activity.

The concentration of HA was measured in accordance with the following principle: in the presence of an acidic solution of bovine serum albumin, HA precipitates. Thus, in the case of the presence of HA, a precipitate is formed and in the case of complete hydrolysis of the HA, no precipitate is observed. Thus, the quantity of precipitation is propotion& to the HA content.

The reaction mixture (RM) was as follows: solution of hyaluronic acid [0.03% (w/v)] in the 300 mM phosphate buffer, pH 5.35: 187.5 µL; 50 mM phosphate buffer, pH 7: 52.5 µL; solution containing the extract or the solvent (white): 10 µL. The enzymatic conversion was initialized by adding a volume of 250 µL of hyaluronidase originating from bull testicles (type IV-S) to the 50 mM phosphate buffer, pH 7 (20 µg/mL, activity between 15 and 60 U/mL). This mixture was incubated at 37° C., with stirring (using a vortex mixer) throughout the duration of the enzymatic reaction.

In order to follow the enzymatic degradation of the HA, a volume of 50 µl of RM was removed every 15 minutes, mixed with a volume of 250 µL of the solution of acidic BSA (acidic solution of bovine serum albumin: 24 mM sodium acetate, 79 mM acetic add and 0.1% (w/v) bovine serum albumin, pH 3.75) then incubated for 10 min at ambient temperature. The quantity of precipitate formed was then measured using a plate reader (diffusion of light at 600 nm).

The root extract of *Morus alba* prepared in accordance with Example 5 strongly inhibited the activity of hyaluronidase: for 1% (v/v) of extract, a 100% inhibition was observed; at 0.5% (v/v) of extract, an inhibition of 55.5% was observed, and at 0.1% (v/v) of extract, an inhibition of 34.5% was observed.

The measurement of the anti-hyaluronidase inhibiting activity of moracenin A was carried out in accordance with the same protocol as that of Example 5.

At a concentration of 10 µM, an inhibition of 55.1% was observed. This inhibiting activity of moracenin A was stronger than that of quercetin, a known inhibitor of hyaluronidase (15.6% inhibition at a concentration of 10 µM).

6.2 Evaluation of the Affinity of the Compounds Present in a Root Extract of Non-Stimulated *M. Alba* for the Hyaluronidase Target: Affinity Test By Target Binding®

A root extract of *Morus Alba* was prepared in accordance with the protocol described in Example 2.1. The Target Binding® method used was that of Example 2.3 which is described in patent application FR 1 670 545. The experimental protocol was as follows: The target, a 5 mg/mL solution of hyaluronidase, was prepared by dissolving powdered lyophilized enzyme in 50 mM sodium phosphate, with a pH of 7.0. The extract corresponded to the supernatant obtained in accordance with Example 2.1. It could optionally be centrifuged once again before use, at 21000 g for 15 min, in order to eliminate the solid particles before use. A reference sample was also prepared by diluting the sample 10-fold in a solution of water and a quarter of the volume of acetonitrile.

The steps of the method were as follows:
1. Preconditioning step—Wells with a filtering membrane were preconditioned with a volume of 500 µL of a solution of 50 mM sodium phosphate, at a pH of 7.0 which was passed through the membrane by centrifuging at 14000 g for 60 seconds.

2. Binding step—The hyaluronidase preparation (5 mg/mL) was mixed with 7.5 µL of the root extract for 5 min in a plastic Eppendorf tube.

3. Washing step—the mixture of the enzyme and the root extract was deposited in a well that had been preconditioned in the preconditioning step, then centrifuged at 14000 g until most of the solvent had been eliminated. The enzyme-ligand complexes remained on the surface of the membrane of the filter then were re-suspended in a volume of 100 µL of the same solution of 50 mM sodium phosphate at a pH of 7.0, and centrifuged at 14000 g until the solvent had been eliminated. This procedure was repeated three times and eliminated all of the compounds that were not bound to the enzyme.

4. Separation step—The enzyme-ligand complexes retained in the filter were re-suspended in a volume of 10 µL of ultra-pure water then mixed with a volume of 40 µL of acetonitrile in order to denature and precipitate the enzyme and at the same time to liberate the ligands. The mixture was centrifuged at 21000 g for 10 min in order to separate the precipitate from the supernatant.

5. Analysis step—Said supernatant was analyzed by liquid phase chromatography coupled to a mass spectrometer, also known by the acronym UPLC-MS. The reference sample was also analyzed in the same manner, using the same analytical conditions.

The UPLC-MS analysis was carried out in accordance with the protocol described in Example 1.

Figures 6A, 6B:
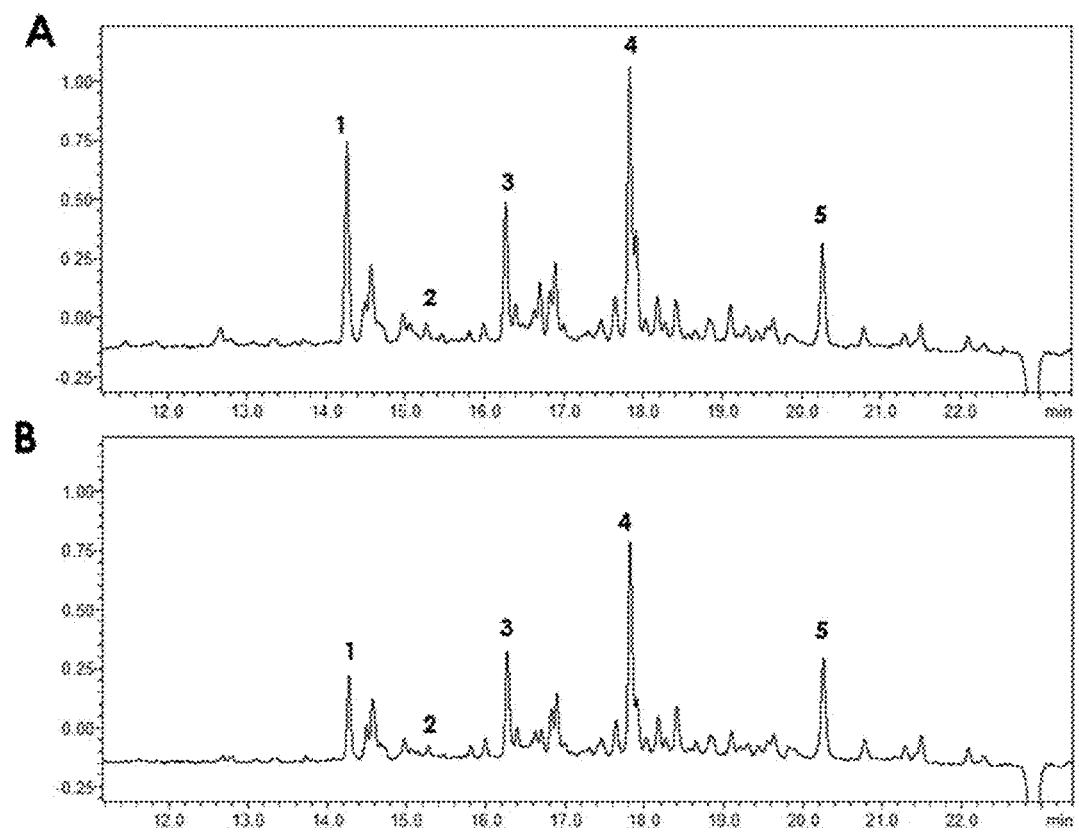
FIGS. 6A and 6B: Chromatograms (UV at 290 nm) for a reference sample (FIG. 6A) and the supernatant obtained in accordance with Example 6.2 during the evaluation of the affinity of a non-stimulated root extract of *M. alba* for hyaluronidase, using the method known as Target Binding® described in patent application FR 1 670 545 (FIG. 6B).

The chromatogram (FIG. 6A) of the reference sample could be used to identify the major compounds present in the root extract in accordance with Example 2.1, namely:

1—moracenin B;

2—kuwanon C;

3—moracenin A;

4—wittiorumin F;

5—mulberrofuran T;

The size of the areas of the peaks of the chromatogram of FIG. 6B obtained after binding the compounds of the extract to the collagenase could be used to demonstrate a similar affinity of mulberrofuran T, wittiorumin F and moracenin A and B for hyaluronidase.

In order to validate this result, the relative affinities were calculated using the method of Example 2.3 and described in patent application FR 1 670 545.

TABLE 9

Relative affinity of moracenin B (considered to be the reference ligand), moracenin A, kuwanon C, wittiorumin F and mulberrofuran T present in the root extract of *M. alba* for hyaluronidase.

Relative affinity (RA) for hyaluronidase

| Moracenin B (ref) | Kuwanon C | Moracenin A | Wittiorumin F | Mulberrofuran T |
|---|---|---|---|---|
| 1.0 | 1.2 | 1.9 | 2.1 | 2.7 |

The relative affinities for hyaluronidase are similar for the 5 compounds.

Example 7

Characterization of a Root Extract of *Morus Alba* as Regards a Benefit to the Skin—Identification of Targets by Analysis of Modifications to the Expression of Genes by QRT-PCR on Taqman Cards The study consisted of measuring the effects of the root extract of *Morus alba* by qRT-PCR on microfluidic TaqMan cards on the one hand on the expression of 94 genes involved in the biology of the dermis, remodeling of conjunctive tissues and aging ("Dermal Benefits" card defined by StratiCELL), and on the other hand on the expression of 94 genes involved in the key functions of the epidermis, such as the barrier function linked directly to hydration, the antioxidant response, or in fact pigmentation by the melanocytes ("Epidermal Benefits" card defined by StratiCELL).

The protocol consisted of adding root extract of *Morus alba* to the culture medium for NHDF (Normal Human Dermal Fibroblasts) as a monolayer and melanized reconstituted human epidermis (RHE/MEL/001), and, after 24 h, analyzing the various RNA populations in order to identify the differentially expressed genes by qRT-PCR.

A prior cytotoxicity study enabled the working concentration for the root extract of *Morus alba* to be defined for the gene expression study. TGF-β1 (Transforming Growth Factor-beta-1) and vitamin D3 (1 a,25-dihydroxyvitamin D3), the effects of which are documented in the literature, were used as reference molecules in order to validate the test systems and the method of analysis.

7.1 Method and Apparatus

Extract

The *Morus alba* plants were cultivated aeroponically with stimulation by nitrogen deficiency with the 0/15/40 medium. The fresh roots were chopped then macerated at ambient temperature for 48 hours in a 70/30 hydroethanolic solution (ethanol/water—v/v) in a ratio of 500 g of roots per liter of solvent and at a pH that was not adjusted. Next, the extract was filtered. The solvent was eliminated using a rotary evaporator and the powder was dried in a desiccator. The moracenin B was assayed in the extract using three 4-point series of moracenin B purified by the Applicant in accordance with the protocol described in Example 1. A 1 mM solution, then dilutions up to 16 μM, were produced in 70% DMSO. The UPLC analysis was carried out on these series. The areas of the peaks corresponding to moracenin B in the extract were then compared with the areas of the peaks of the series. The moracenin B content in the extract corresponded to 4% dry extract.

Cell Culture

The first part of the study was carried out on human dermal fibroblasts, NHDFs (ATCC, CRL-2522, origin: foreskin) cultured in a monolayer in DMEM medium (Invitrogen, 31885-049) containing antibiotics (Penicillin/Streptomycin, Invitrogen, 15140-122) but not containing serum. These were maintained in a moist atmosphere at 37° C. containing 5% $CO_2$. The second part of the study was carried out on reconstituted epidermis (StratiCELL®, RHE/MEL/001) containing or not containing primary human melanocytes, NHEMs (Normal Human Epidermal Melanocytes) originating from a donor with a dark phototype (phototype IV to V) (Invitrogen, C2025C, batch No. 439684). The tissues were cultured at the air-liquid interface for 14 days in a suitable culture medium and a moist atmosphere at 37° C. containing 5% $CO_2$.

**Determination of the Range of Concentrations for the Study of the Root Extract of *Morus Alba* by a Preliminary Cytotoxicity Study**

In order to determine the optimal concentration for analysis for the root extract of *Morus alba*, a preliminary experiment was carried out on NHDF fibroblasts, on NHEM human melanocytes and on reconstituted epidermis.

The NHDF fibroblasts had carried out 30.1 and 30.7 population doublings and the NHEM melanocytes were seeded into 24-well plates 24 h before application of the active agents.

The reconstituted epidermis (RHE/001; batch CB0314/2) was transferred to a 12-well plate before being treated with the extract.

The extract was diluted in the culture medium, then added, without prior filtration, to the culture medium for the NHDF human fibroblasts containing no serum, to the NHEM primary human melanocytes or to the culture medium for the differentiated epidermis.

This study consisted of evaluating the viability of cells and of the epidermis to MTS (3-(4,5-di methythiazol-2-yl)-5-(3-carboxy-methoxyphenyl)-2-(4-sulfophenyl)-2H-tetrazolium) (Promega,G3581), 24 hours after adding the root extract of *Morus alba* and carried out for 5 concentrations and 3 repetitions (n=3) for the NHDF fibroblasts and the NHEM melanocytes, and carried out for 2 concentrations and 3 repetitions (n=3) for the reconstituted epidermis. The 2 concentrations tested for the reconstituted epidermis were selected on the basis of the cytotoxicity results obtained for the NHEM melanocytes.

SDS (sodium dodecyl sulfate) is toxic to the cells and was used as a positive control in order to validate the experiment.

At the end of this experiment, a non-cytotoxic concentration had been defined in order to proceed to the measurement of the modifications to the expression of the target genes.

The following concentrations, in μg of dry extract/mL, were tested:

NHDF fibroblasts and NHEM melanocytes: 0.16 μg/mL, 0.8 μg/mL, 4 μg/mL, 20 μg/mL, 100 μg/mL;

reconstituted epidermis: 20 μg DE/mL and 4 μg DE/mL

Analysis of Modifications to Gene Expression

The extract was added, at a selected concentration, to the culture medium for the human NHDF fibroblasts (having carried out 30.5 and 30.8 population doublings) in the absence of serum or to the culture medium for the melanized differentiated epidermis (RHE/MEL/001, batches CB0314/3 and CB0314/4), without filtration prior to contact with the cells/epidermis. Reference molecules were studied at the same time, namely TGFβ1 for the NHDF fibroblasts and vitamin D3 (VD3) for the reconstituted epidermis.

Extraction of Total RNA

The extraction of the total RNA was carried out with the aid of the RNeasy Mini kit (Qiagen, 74106). 24 h after adding the extract, the cells were rinsed with PBS and lysed in the ad hoc lysis buffer, while the epidermis was immersed directly in this buffer (culture was carried out in triplicate for each condition). The extraction and purification of the RNA was then carried out in accordance with the instructions of the supplier. The total RNA was then preserved at −80° C.

Qualification of RNA by Spectrophotometry and Capillary Electrophoresis

The concentration of the total RNA was determined by spectrophotometric measurement. The quality and the integrity of the RNA were then verified by capillary electrophoresis (Agilent Bioanalyzer 2100 platform—Agilent RNA 6000Nano Kit, 5067-1511).

Quantification of RNA by spectrophotometric measurement: an aliquot of each RNA was diluted in RNase-free water and its concentration was determined with the aid of an Ultrospec 1100 Pro spectrophotometer (Amersham).

Integrity of RNA by capillary electrophoresis on Agilent Bioanalyzer: the integrity of the total RNA was evaluated by viewing the electrophoresis corresponding peaks corresponding to ribosomal RNA. For the total RNA for higher eukaryotes, the size of the ribosomal bands must be 1.9 kb for 18S-RNA and 4.7 kb for 28S-RNA. The intensity of the band corresponding to 28S-RNA must be higher than the intensity of the band corresponding to 18S-RNA. Small diffuse bands representing RNA with a lower molecular weight (tRNA and 5S ribosomal RNA) may be present. When the RNA is degraded, spreading of the bands for ribosomal RNA is observed, as well as a background noise of RNA with a higher molecular weight.

Synthesis of Complementary DNA or cDNA

Reverse transcriptions (RT) were carried out with the aid of the "High Capacity RNA-to-cDNA Kit" (Applied Biosystems, 4387406). For the synthesis of cDNA, a mixture was prepared in accordance with the instructions from the supplier, with 2 µg of total RNA, the ad hoc buffer provided in the kit and the enzyme, reverse transcriptase. This reaction was carried out at 37° C. for 1 hour, then 5 minutes at 95° C., and finally the cDNA samples were placed on ice and stored at −20° C.

Validation of Test Systems—Real Time qPCR with the Aid of Fluorescent TaqMan Type Probes The real time qPCR method was used to quantify the expression of various specific targets in the populations of RNA obtained from NHDF fibroblasts treated with TGF-β1 (20 ng/mL) as well as melanized epidermis treated with vitamin D3 (100 nM) and with the solvent ethanol (EtOH 0.1%), used to dissolve the VD3.

The target sequences for the genes of interest were amplified by PCR by using "TaqMan Gene Expression Assays" (Applied Biosystems). These kits comprise a TaqMan probe and 2 specific primers, which have been pre-mixed in a concentration of 18 µM for each primer and 5 µM for the probe. This mixture was concentrated 20-fold. The TaqMan probes were grafted with a fluorophore (FAM) at the 5' end of the sequence and with a fluorescence "quencher" at the 3' end.

The PCRs were carried out with the aid of the 7900HT Fast Real-Time PCR system (Applied Biosystems). The reactions were carried out in a volume of 20 µL. The reaction mixture contained 10 µL of TaqMan Fast Universal Master Mix (Applied Biosystems), 1 µL of TaqMan Gene Expression Assay and 5 µL of RNase-free water.

16 µL of mixture and 4 µL of cDNA (4 ng) was added to each well of a 96-well microplate. For the purposes of normalization, the reaction mixtures with the probes and primers, corresponding to glyceraldehyde-3-phosphate dehydrogenase (GAPDH) for the fibroblasts and to β2-microglobulin (B2M) for the melanized epidermis, were also prepared with the same cDNA samples. A control without cDNA acted as the negative amplification control. The thermal cycles were programmed with a step for incubation at 50° C. for 2 min, followed by a first step for denaturing at 95° C. for 10 min. The PCR amplification protocol was continued with 40 cycles of 15 seconds at 95° C. followed by one minute at 60° C.

The expression levels were quantified using the method for calculating the relative expression with respect to a housekeeping gene ($2^{-\Delta Ct}$), derived from the calculation of ΔΔCt (Pfaffl, A new mathematical model for relative quantification in real-time RT-PCR, Nucleic Acids Res, 29 (9), 2001, 2002-2007; Livak and Schmittgen, Analysis of relative gene expression data using Real-Time Quantitative PCR and the $2^{-\Delta Ct}$ method, Methods, 25 (4), 2001, 402-408) described below:

The relative quantification of the transcripts was carried out using a calculation method that consists of comparing the mean of the control values (Ct) obtained for the TGF-β1 (20 ng/mL) and VD3 (100 nM) conditions with the respective control conditions (untreated CTL and CTL Ethanol 0.1%). These Cts represent the detection threshold from which the quantity of DNA is such that the signal can be significantly distinguished from the background noise. This mean value for Ct was normalized with respect to a housekeeping gene, namely glyceraldehyde-3-phosphate dehydrogenase (GAPDH) for the NHDF fibroblasts and β2-microglobulin (B2M) for the melanized reconstituted epidermis. Thus, the difference in the expression level (RQ) was obtained using the formula:

$$RQ = 2^{-(\Delta Ct\ treated\ condition - \Delta Ct\ reference\ condition)}$$

where ΔCt=Ct (target gene)−Ct (housekeeping gene) in the same sample of cDNA.

Preparation of Taqman Microfluidic Cards, Carrying Out Quantitative PCR and Analysis of Ct The reaction mixtures for PCR on TaqMan microfluidic cards, produced to order by Applied Biosystems, were prepared by following the detailed instructions in the Applied Biosystems Micro Fluidic Card Getting Started Guide. In summary, 100 ng of cDNA was added to a specific mixture for PCR (Taqman Universal PCR Master Mix, 4364338, Applied Biosystems) before being injected into the card and dispersed by capillarity. After having centrifuged the card, this was sealed before carrying out the quantitative PCR and the analysis with the 7900HT system from Applied Biosystems, with the aid of ABI PRISM® 7900 Sequence Detection System software, SDS2.4.

The threshold cycles (Ct) were obtained for all of the genes represented on the cards and expressed by the NHDF fibroblasts and by melanized reconstructed epidermis.

The results were exported from the real time qPCR instrument using SDS RQ Manager software (v1.2.1, Applied Biosystems) and the analysis of the modifications to expression was carried out with the aid of Data Assist software (V3.0., Applied Biosystems) designed to carry out the relative quantification of gene expression using the Ct comparison method (ΔΔCt) (Pfaffl, 2001 and Livak and Shmittgen, 2001) described in the paragraph above and a combination of statistical analyses. As described above, the method for calculating the ΔΔCt consists of comparing the values for Ct obtained for the conditions treated by the extract with the reference condition (DMSO control). These values for Ct have themselves been normalized with respect to the housekeeping gene GAPDH (glyceraldehyde-3-phosphate dehydrogenase) for the NHDF fibroblasts and B2M (β-2 microglobulin) for the melanized reconstructed epidermis. The maximum admissible value for Ct used as the detection threshold was fixed at 36 cycles.

7.2 Results 7.2.1 Determination of the Concentration for Analysis of the Extract by a Cytotoxicity Study The prior cytotoxicity study on NHDF fibroblasts, on human NHEM melanocytes and on reconstituted epidermis allowed a working concentration (prepared in DMSO) to be defined for the gene expression study. The solvent present in the extract was tested at the same time. SDS at 0.08% (for NHDF) and at 0.05% (for NHEM) was used as the positive cytotoxicity control in order to validate the experiment. Based on these results (data not shown), the following concentrations were selected for the rest of the study: 20 µg of dry extract/mL for the NHDF fibroblasts and 20 µg of dry extract/mL for the melanized reconstituted epidermis.

7.2.2 Qualification of RNA by Capillary Electrophoresis

The various RNA populations display the presence of narrow peaks well, corresponding to 18S and 28S ribosomal RNA, and a balanced ratio between the two peaks. The absence of intermediate and broad peaks, characteristics of RNA degradation products, is evidence of the integrity of the various populations (data not shown). The quality and integrity of the RNA extracts having been demonstrated, these were then used for the remainder of the protocol and engaged in the reactions for the synthesis of complementary DNA.

7.2.3 Effects of the Extract on 94 Target Genes in NHDF Fibroblasts

The extract was added to the culture medium for the NHDF fibroblasts (n=3). The controls treated only with the 1% DMSO solvent (vehicle for the extract) were also analyzed. At the same time, TGF-β1 (20 ng/mL) was studied as a validation control. After 24 hours of culture of the NHDF fibroblasts, the total RNA populations were extracted, their integrity was analyzed by capillary electrophoresis, and the differences in gene expression were analyzed by qRT-PCR with the aid of 96-well TaqMan cards, targeting the key functions of the dermis.

Afterwards, the regulations observed as a link with these hypotheses were recorded as follows: the symbol for the genes, the name of the genes, the relative expression (RQ) with respect to the 1% DMSO vehicle (RQ>1: increase) and the value of p (p-value).

Structure and Homeostasis of the Extracellular Matrix (ECM)

The root extract of *Morus alba* induces the expression of the COL3A1 gene which codes for the alpha-1 sub-unit of type III collagen (X 1.5, p=0, 0172). The fibrillar collagens are by far the most abundant proteins in the skin, constituting more than 90% of its dry weight. Type I collagen represents 60% to 80% of the collagens of the dermis and the hypodermis, while type III collagen (COL3A1) accounts for 15% to 25% and type V collagen for 2% to 5%. The type I, III and V collagens self-assemble into thicker fibers in order to form a three-dimensional network throughout the thickness of the dermis. Hence, collagen III (COL3A1) plays a role in the structure at the ECM and thus in the strength and elasticity of the dermis.

Induction of the COL3A1 gene by the extract could prove to be interesting with a view to an anti-aging strategy in order to allow a reduction in the degradation of the dermis with age.

The root extract of *Morus alba* induces a reduction in the expression of the gene for metalloproteinase-1, MMP-1 (X 0.66, p-value=0.0066). The fibroblasts secrete collagenases (or MMP, metalloproteinases) and inhibitors of matrix proteases in order to degrade the extracellular matrix, renew it and reorganize it. The metalloproteinase 1 (MMP1) initiates the cleavage of fibrils of type I and III collagen in the skin.

In this context, the extract proves to be interesting in reducing the degradation of the dermis with age. In fact, it promotes the expression of type III collagen while reducing the expression of MMP-1.

Skin Healing

The root extract of *Morus alba* induces the expression of the ACTA2 gene coding for actin (X 1.17, p-value=0.04) and plays an important role in the differentiation of the fibroblast into a myofibroblast during healing.

7.2.4 Effects of the Extract on 94 Target Genes in Melanized Reconstructed Epidermis (RHE/MEL/001)

The 20 µg DE/mL extract was applied to reconstructed epidermis for 24 hours. Controls treated only with 0.2% DMSO solvent (vehicle for the extract) were also analyzed. The symbol for the genes, the name of the genes, the relative expression (RQ) with respect to the 0.2% DMSO vehicle (RQ>1: increase; RQ<1: reduction) and the p-value are presented.

Barrier Function of the Epidermis

The root extract is an inducer of the expression of the HRNR gene (hornerin) with an amplitude of 3.9 (p-value=0.0011). Hornerin is a protein present in the stratum corneum and the stratum granulosum of the epidermis. It is an essential protein in the mechanical strength of the stratum corneum. Because of its positive effect on the expression of hornerin, essential to the stratum corneum and the stratum granulosum of the epidermis, the extract plays a positive role in the integrity and effectiveness of the barrier function of the epidermis.

Skin Healing

The root extract of *Morus alba* induced the expression of the gene for metalloproteinase-1, MMP-1, in an amplitude of 2.1 (p-value=0.0289). MMPs are metalloproteinases capable of cleaving the majority of the components of the ECM and of modifying, by proteolysis, a large number of molecules which are important for skin healing. In particular, MMP1 plays a major role in the re-epithelialization of keratinocytes. MMP1 facilitates the assembly of the ECM, elongation and migration of cells, reorganization of the actin cytoskeleton, and induces the activation of the kinase ERK (extracellular signal-regulated kinase) which is necessary to the motility and the invasion capability of epithelial cells. Furthermore, it has been shown that the MMP1 protein is over-expressed in the epidermis in response to skin wounds.

The overexpression of the MMP-1 gene in the epidermis by the root extract of *Morus alba* means that it has a role to play as an active agent that potentially promotes skin healing, in particular at the level of closing of a wound.

Depigmentation Effect

In turn, the POMC gene is reprimed (X 0.3, p-value=0.0175). It codes for proopiomelanocortin, a precursor protein of several pituitary hormones including alpha-MSH (alpha-melanocyte-stimulating hormone) which is known to stimulate melanogenesis. By reducing the expression of POMC, the root extract of *Morus alba* could therefore have a depigmenting effect on the epidermis.

7.3 Conclusion

In summary, the root extract of *Morus alba* clearly has a role to play in cosmetics with a view to anti-aging, i.e. in preventing or retarding the appearance of the effects of aging, linked to a reduction in the degradation of the dermis associated with a positive role in the integrity and effectiveness of the barrier function of the epidermis.

In addition, the root extract of *Morus alba* could have a depigmentation effect on the epidermis.

Finally, the root extract of *Morus alba* could act as an active agent promoting skin healing comprise closing of a wound.

The invention claimed is:

1. A root extract of plants of the genus *Morus*, wherein:
   it comprises at least 2% by weight of moracenin B, expressed with respect to the total weight of the dry extract,
   it comprises moracenin A, in a quantity of at least 0.05% by weight in equivalents of moracenin B, expressed with respect to the total weight of the dry extract,
   it comprises kuwanon C, in a quantity of at least 0.1% by weight in equivalents of moracenin B, expressed with respect to the total weight of the dry extract, and
   it comprises at least one of the following two compounds:
   wittiorumin F, in a quantity of at least 0.1% by weight in equivalents of moracenin B, expressed with respect to the total weight of the dry extract,
   mulberrofuran T, in a quantity of at least 0.1% by weight, expressed with respect to the total weight of the dry extract.

2. The extract as claimed in claim 1, wherein said plant of the genus *Morus* is selected from the group constituted by *Morus alba* and *Morus nigra*.

3. A cosmetic composition comprising, as the active agent, at least one extract as claimed in claim 1, and at least one cosmetically acceptable excipient.

4. A pharmaceutical composition comprising, as the active agent, at least one extract as claimed in claim 1, and at least one pharmaceutically acceptable excipient.

5. A nutraceutical composition comprising, as the active agent, at least one extract as claimed in claim 1, and at least one nutraceutically acceptable excipient.

6. The root extract of plants of the genus *Morus* of claim 1, comprising: at least 2.3% by weight of moracenin B; moracenin A, in a quantity of at least 0.5% by weight in equivalents of moracenin B; kuwanon C, in a quantity of at least 0.5% by weight in equivalents of moracenin B; and at least one of the following two compounds:
   wittiorumin F, in a quantity of at least 0.4% by weight in equivalents of moracenin B; and
   mulberrofuran T, in a quantity of at least 0.3% by weight.

7. The root extract of plants of the genus *Morus* of claim 1, comprising: at least 4% by weight of moracenin B; moracenin A, in a quantity of at least 2% by weight in equivalents of moracenin B; kuwanon C, in a quantity of at least 1% by weight in equivalents of moracenin B; and at least one of the following two compounds:
   wittiorumin F, in a quantity of at least 0.5% by weight in equivalents of moracenin B; and
   mulberrofuran T, in a quantity of at least 0.4% by weight.

8. A cosmetic composition comprising, as the active agent, at least one extract as claimed in claim 2, and at least one cosmetically acceptable excipient.

9. A pharmaceutical composition comprising, as the active agent, at least one extract as claimed in claim 2, and at least one pharmaceutically acceptable excipient.

10. A nutraceutical composition comprising, as the active agent, at least one extract as claimed in claim 2, and at least one nutraceutically acceptable excipient.

11. The extract as claimed in claim 1, wherein said extract is obtained by a method comprising at least one step of solid/liquid extraction of roots of plants of the genus *Morus* cultured under soil-free conditions.

12. A method for the preparation of a root extract from plants of the genus *Morus* as claimed in claim 1, comprising:
   a) a step for culturing plants of the genus *Morus* under soil-free conditions
   b) a step for stimulation of the roots of the plants,
   c) a step for solid/liquid extraction of the roots, and
   d) recovery of the extract obtained during step c).

13. The method as claimed in claim 12, in which step c) comprises chopping, drying and crushing said roots, followed by maceration of the crushed roots in a solvent, said solvent being selected from alcohols, glycols and eutectic solvents, and being used pure or in the form of an aqueous solution of alcohol, glycol or eutectic solvent.

14. A method to promote skin healing, comprising providing the extract of claim 1, and applying an effective amount of the extract to the skin.

15. A method to prevent or retard the appearance of the effects of aging of the skin and/or intended to have a whitening effect on the skin, comprising preparing a cosmetic composition comprising the extract of claim 1, and applying an effective amount of the cosmetic composition to the skin.

16. The method of claim 12, wherein step a) is performed aeroponically.

17. A method to promote skin healing, comprising providing the extract of claim 2, and applying an effective amount of the extract to the skin.

18. A method to promote skin healing, comprising providing the pharmaceutical composition as claimed in claim 4, and applying an effective amount of the extract to the skin.

19. A method to promote skin healing, comprising providing the nutraceutical composition as claimed in claim 5, and applying an effective amount of the extract to the skin.

20. A method to prevent or retard the appearance of the effects of aging of the skin and/or intended to have a whitening effect on the skin, comprising preparing a cosmetic composition comprising the extract of claim 2, and applying an effective amount of the cosmetic composition to the skin.

21. A method for the preparation of a root extract from plants of the genus *Morus* as claimed in claim 2, comprising:
   a) a step for culturing plants of the genus *Morus* under soil-free conditions
   b) a step for stimulation of the roots of the plants,
   c) a step for solid/liquid extraction of the roots, and
   d) recovery of the extract obtained during step c).

* * * * *